US012279956B2

(12) United States Patent
Siegel et al.

(10) Patent No.: US 12,279,956 B2
(45) Date of Patent: Apr. 22, 2025

(54) METHOD AND APPARATUS FOR PERCUTANEOUS DELIVERY AND DEPLOYMENT OF A CARDIAC VALVE PROSTHESIS

(71) Applicant: CEDARS-SINAI MEDICAL CENTER, Los Angeles, CA (US)

(72) Inventors: Robert James Siegel, Beverly Hills, CA (US); Lawrence E. Ong, Beverly Hills, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 171 days.

(21) Appl. No.: 16/999,827

(22) Filed: Aug. 21, 2020

(65) Prior Publication Data
US 2021/0030534 A1 Feb. 4, 2021

Related U.S. Application Data

(62) Division of application No. 15/510,617, filed as application No. PCT/US2015/049251 on Sep. 9, 2015, now Pat. No. 10,799,359.
(Continued)

(51) Int. Cl.
*A61F 2/24* (2006.01)
*A61B 17/12* (2006.01)
(Continued)

(52) U.S. Cl.
CPC ........ *A61F 2/246* (2013.01); *A61B 17/12036* (2013.01); *A61B 17/12122* (2013.01);
(Continued)

(58) Field of Classification Search
CPC .................. A61F 2/246; A61F 2/2466; A61F 2220/0091; A61F 2230/0054;
(Continued)

(56) References Cited

U.S. PATENT DOCUMENTS 4,777,951 A  10/1988  Cribier
5,171,259 A  12/1992  Inoue
(Continued)

FOREIGN PATENT DOCUMENTS

CN  106175986  12/2016
EP  1 674 040  6/2006
(Continued)

OTHER PUBLICATIONS

Bhargava et al., "Biosense Left Ventricular Electromechanical Mapping", Asian Cardiovasc Thorac Ann 1999, 7:345-52.
(Continued)

*Primary Examiner* — Brooke Labranche
(74) *Attorney, Agent, or Firm* — Knobbe, Martens, Olson & Bear, LLP

(57) ABSTRACT

Catheter apparatuses and methods are provided for repairing heart valves, particularly mitral valves. The method includes providing a catheter having an elongate, flexible body, with a proximal end and a distal end. The distal end can be transluminally advanced from the left atrium through the mitral valve. A distal anchor zone or portion coupled with the proximal end can extend and along the left ventricular outflow tract into the ascending aorta. A valve repair device is deployed to permanently connect leaflets at a mid-section of a mitral valve while permitting medial and lateral portions of the natural leaflets to open and close. The catheter apparatuses may be positionable using a steering device. The valve repair device detachably connects the distal and proximal ends of the catheter. The valve repair device can be detached using low profile devices actuatable from the proximal or distal ends, e.g., at a venous or arterial access site.

19 Claims, 28 Drawing Sheets

Related U.S. Application Data

(60) Provisional application No. 62/048,732, filed on Sep. 10, 2014.

(51) Int. Cl.
*A61B 17/122* (2006.01)
*A61B 17/128* (2006.01)
*A61B 17/00* (2006.01)
*A61B 17/22* (2006.01)

(52) U.S. Cl.
CPC ........ *A61B 17/122* (2013.01); *A61B 17/1227* (2013.01); *A61B 17/1285* (2013.01); *A61F 2/2466* (2013.01); *A61B 2017/00243* (2013.01); *A61B 2017/00292* (2013.01); *A61B 2017/00535* (2013.01); *A61B 2017/00539* (2013.01); *A61B 2017/00544* (2013.01); *A61B 2017/00783* (2013.01); *A61B 2017/22038* (2013.01)

(58) Field of Classification Search
CPC ........ A61B 17/12036; A61B 17/12122; A61B 17/122; A61B 17/1227; A61B 17/1285; A61B 2017/00243; A61B 2017/00292; A61B 2017/00535; A61B 2017/00539; A61B 2017/00544; A61B 2017/00783; A61B 2017/22038
See application file for complete search history.

(56) References Cited

U.S. PATENT DOCUMENTS

| | | |
|---|---|---|
| 5,201,880 A | 4/1993 | Wright et al. |
| 5,573,540 A | 11/1996 | Yoon |
| 5,575,799 A | 11/1996 | Bolanos et al. |
| 5,609,598 A | 3/1997 | Laufer et al. |
| 5,626,588 A | 5/1997 | Sauer et al. |
| 5,716,367 A | 2/1998 | Koike et al. |
| 6,029,671 A | 2/2000 | Stevens et al. |
| 6,051,014 A | 4/2000 | Jang |
| 6,090,096 A | 7/2000 | St. Goar et al. |
| 6,117,144 A | 9/2000 | Nobles et al. |
| 6,117,145 A | 9/2000 | Wood et al. |
| 6,136,010 A | 10/2000 | Modesitt et al. |
| 6,165,183 A | 12/2000 | Kuehn et al. |
| 6,197,043 B1 | 3/2001 | Davidson |
| 6,206,893 B1 | 3/2001 | Klein et al. |
| 6,269,819 B1 | 8/2001 | Oz et al. |
| 6,287,321 B1 | 9/2001 | Jang |
| 6,312,446 B1 | 11/2001 | Huebsch et al. |
| 6,312,447 B1 | 11/2001 | Grimes |
| 6,325,067 B1 | 12/2001 | Sterman et al. |
| 6,328,757 B1 | 12/2001 | Matheny |
| 6,461,366 B1 | 10/2002 | Seguin |
| 6,508,828 B1 | 1/2003 | Akerfeldt et al. |
| 6,575,971 B2 | 6/2003 | Hauck et al. |
| 6,629,534 B1 | 10/2003 | Goar et al. |
| 6,635,068 B1 | 10/2003 | Dubrul et al. |
| 6,752,813 B2 | 6/2004 | Goldfarb et al. |
| 6,770,083 B2 | 8/2004 | Seguin |
| 6,926,715 B1 | 8/2005 | Hauck et al. |
| 6,932,792 B1 | 8/2005 | St. Goar et al. |
| 6,945,978 B1 | 9/2005 | Hyde |
| 7,048,754 B2 | 5/2006 | Martin et al. |
| 7,226,467 B2 | 6/2007 | Lucatero et al. |
| 7,276,078 B2 | 10/2007 | Spenser et al. |
| 7,404,824 B1 | 7/2008 | Webler et al. |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,632,308 B2 | 12/2009 | Loulmet |
| 7,635,329 B2 | 12/2009 | Goldfarb et al. |
| 7,666,204 B2 | 2/2010 | Thornton et al. |
| 7,704,269 B2 | 4/2010 | St. Goar et al. |
| 7,736,388 B2 | 6/2010 | Goldfarb et al. |
| 7,811,296 B2 | 10/2010 | Goldfarb et al. |
| 7,828,819 B2 | 11/2010 | Webler et al. |
| 7,854,762 B2 | 12/2010 | Speziali et al. |
| 7,938,827 B2 | 5/2011 | Hauck et al. |
| 7,981,123 B2 | 7/2011 | Seguin |
| 8,052,592 B2 | 11/2011 | Goldfarb et al. |
| 8,123,703 B2 | 2/2012 | Martin et al. |
| 8,172,856 B2 | 5/2012 | Eigler et al. |
| 8,216,256 B2 | 7/2012 | Raschdorf, Jr. et al. |
| 8,216,302 B2 | 7/2012 | Wilson et al. |
| 8,303,608 B2 | 11/2012 | Goldfarb et al. |
| 8,323,334 B2 | 12/2012 | Deem et al. |
| 8,382,796 B2 | 2/2013 | Blaeser et al. |
| 8,409,219 B2 | 4/2013 | Kelley et al. |
| 8,409,273 B2 | 4/2013 | Thornton et al. |
| 8,545,551 B2 | 10/2013 | Loulmet |
| 8,568,472 B2 | 10/2013 | Marchand et al. |
| 8,920,463 B2 | 12/2014 | McGukin, Jr. et al. |
| 8,932,325 B2 | 1/2015 | Stanley et al. |
| 8,992,605 B2 | 3/2015 | Zakai et al. |
| 9,023,099 B2 | 5/2015 | Duffy et al. |
| 9,060,858 B2 | 6/2015 | Thornton et al. |
| 9,474,605 B2 | 10/2016 | Rowe et al. |
| 9,498,330 B2 | 11/2016 | Solem |
| 9,763,658 B2 | 9/2017 | Eigler et al. |
| 10,080,657 B2 | 9/2018 | Siegel |
| 10,105,221 B2 | 10/2018 | Siegel |
| 10,478,304 B2 | 11/2019 | McNiven et al. |
| 10,499,905 B2 | 12/2019 | Eigler et al. |
| 10,758,241 B1 | 9/2020 | Lashinski et al. |
| 10,758,265 B2 | 9/2020 | Siegel |
| 10,799,359 B2 | 10/2020 | Siegel et al. |
| 10,898,323 B2 | 1/2021 | Siegel |
| 11,241,308 B2 | 2/2022 | Siegel et al. |
| 11,291,544 B2 | 4/2022 | Siegel et al. |
| 11,439,501 B2 | 9/2022 | Siedel et al. |
| 11,653,948 B2 | 5/2023 | Siegel |
| 11,730,591 B2 | 8/2023 | Siegel et al. |
| 2001/0005787 A1 | 6/2001 | Oz et al. |
| 2002/0013571 A1 | 1/2002 | Goldfarb et al. |
| 2002/0183787 A1 | 12/2002 | Wahr et al. |
| 2003/0120340 A1 | 6/2003 | Liska et al. |
| 2004/0044350 A1 | 3/2004 | Martin et al. |
| 2004/0260322 A1 | 12/2004 | Rudko et al. |
| 2005/0033446 A1 | 2/2005 | Deem et al. |
| 2005/0107871 A1 | 5/2005 | Realyvasquez et al. |
| 2005/0143811 A1 | 6/2005 | Realyvasquez |
| 2005/0222489 A1 | 10/2005 | Rahdert et al. |
| 2005/0273135 A1 | 12/2005 | Chanduszko et al. |
| 2006/0004442 A1 | 1/2006 | Spenser et al. |
| 2006/0020275 A1 | 1/2006 | Goldfarb et al. |
| 2006/0074484 A1 | 4/2006 | Huber |
| 2006/0089671 A1 | 4/2006 | Goldfarb et al. |
| 2006/0229708 A1 | 10/2006 | Powell et al. |
| 2006/0241745 A1 | 10/2006 | Solem |
| 2006/0293739 A1 | 12/2006 | Vijay |
| 2007/0032850 A1 | 2/2007 | Ruiz et al. |
| 2007/0038293 A1 | 2/2007 | St.Goar et al. |
| 2007/0055303 A1 | 3/2007 | Vidlund et al. |
| 2007/0093890 A1 | 4/2007 | Eliasen et al. |
| 2007/0198082 A1 | 8/2007 | Kapadia et al. |
| 2007/0255273 A1 | 11/2007 | Fernandez et al. |
| 2007/0270943 A1 | 11/2007 | Solem et al. |
| 2007/0293943 A1 | 12/2007 | Quinn |
| 2009/0048668 A1 | 2/2009 | Wilson et al. |
| 2009/0062836 A1 | 3/2009 | Kurrus |
| 2009/0076600 A1 | 3/2009 | Quinn |
| 2009/0177266 A1 | 7/2009 | Powell et al. |
| 2010/0022823 A1 | 1/2010 | Goldfarb et al. |
| 2010/0217283 A1 | 8/2010 | St.Goar et al. |
| 2010/0298929 A1 | 11/2010 | Thornton et al. |
| 2011/0029071 A1 | 2/2011 | Zlotnick et al. |
| 2011/0066233 A1 | 3/2011 | Thornton et al. |
| 2011/0082495 A1 | 4/2011 | Ruiz |
| 2011/0106245 A1 | 5/2011 | Miller et al. |
| 2011/0137397 A1 | 6/2011 | Chau et al. |
| 2011/0218620 A1 | 9/2011 | Meiri et al. |
| 2011/0224655 A1 | 9/2011 | Asirvatham et al. |

(56) References Cited

U.S. PATENT DOCUMENTS

| | | |
|---|---|---|
| 2011/0264208 A1 | 10/2011 | Duffy et al. |
| 2011/0313437 A1 | 12/2011 | Yeh |
| 2011/0319989 A1 | 12/2011 | Lane et al. |
| 2012/0010700 A1 | 1/2012 | Spenser |
| 2012/0065464 A1 | 3/2012 | Ellis et al. |
| 2012/0078360 A1 | 3/2012 | Rafiee |
| 2012/0095547 A1 | 4/2012 | Chuter |
| 2012/0116418 A1 | 5/2012 | Belson et al. |
| 2012/0191181 A1 | 7/2012 | Kassab et al. |
| 2012/0245678 A1 | 9/2012 | Solem |
| 2012/0310334 A1 | 12/2012 | Dolan |
| 2013/0018414 A1 | 1/2013 | Widimski et al. |
| 2013/0030522 A1 | 1/2013 | Rowe et al. |
| 2013/0066341 A1 | 3/2013 | Ketai et al. |
| 2013/0110227 A1 * | 5/2013 | Quadri ............... A61F 2/2439 623/2.11 |
| 2013/0197559 A1 | 8/2013 | Hariton et al. |
| 2013/0226288 A1 | 8/2013 | Goldwasser et al. |
| 2013/0253547 A1 | 9/2013 | Goldfarb et al. |
| 2013/0261739 A1 | 10/2013 | Kuehn |
| 2013/0297010 A1 * | 11/2013 | Bishop ............... A61F 2/2439 623/2.11 |
| 2013/0338764 A1 | 12/2013 | Thornton et al. |
| 2014/0039607 A1 | 2/2014 | Kovach |
| 2014/0039608 A1 | 2/2014 | Eidenschink |
| 2014/0058502 A1 | 2/2014 | Marchand et al. |
| 2014/0236198 A1 | 8/2014 | Goldfarb et al. |
| 2014/0277426 A1 | 9/2014 | Dakin et al. |
| 2014/0371789 A1 | 12/2014 | Hariton et al. |
| 2015/0038988 A1 | 2/2015 | Tegels et al. |
| 2015/0134057 A1 | 5/2015 | Rourke et al. |
| 2015/0173765 A1 | 6/2015 | Miller et al. |
| 2016/0324635 A1 | 11/2016 | Vidlund et al. |
| 2017/0100250 A1 | 4/2017 | Marsot et al. |
| 2017/0143478 A1 | 5/2017 | Schwartz et al. |
| 2017/0174979 A1 | 6/2017 | Sanders |
| 2017/0216028 A1 | 8/2017 | Khalil |
| 2017/0325842 A1 | 11/2017 | Siegel et al. |
| 2018/0193016 A1 | 7/2018 | Eigler et al. |
| 2018/0289478 A1 | 10/2018 | Quill |
| 2019/0008638 A1 | 1/2019 | Siegel et al. |
| 2019/0076246 A1 | 3/2019 | Siegel |
| 2019/0298516 A1 | 10/2019 | Siegel et al. |
| 2019/0343630 A1 | 11/2019 | Kizuka |
| 2019/0365529 A1 | 12/2019 | Siegel et al. |
| 2020/0030092 A1 | 1/2020 | Tuval et al. |
| 2020/0121454 A1 | 4/2020 | Spence |
| 2020/0367926 A1 | 11/2020 | Siegel |
| 2020/0375730 A1 | 12/2020 | Siegel et al. |
| 2022/0226113 A1 | 7/2022 | Siegel et al. |
| 2023/0050824 A1 | 2/2023 | Siegel et al. |

FOREIGN PATENT DOCUMENTS

| | | |
|---|---|---|
| EP | 1 539 015 | 4/2011 |
| EP | 3 269 330 | 1/2018 |
| JP | H05-220174 | 8/1993 |
| JP | 2004-008805 | 1/2004 |
| JP | 2004-530451 | 10/2004 |
| JP | 2004-531337 | 10/2004 |
| JP | 2008-142563 | 6/2008 |
| JP | 2008-514307 | 8/2008 |
| WO | WO 00/60995 | 10/2000 |
| WO | WO 01/26557 | 4/2001 |
| WO | WO 01 /070116 | 9/2001 |
| WO | WO 02/034167 | 5/2002 |
| WO | WO 03/049619 | 6/2003 |
| WO | WO 2004/012583 | 2/2004 |
| WO | WO 2005/058239 | 6/2005 |
| WO | WO 2007/011994 | 1/2007 |
| WO | WO 2011/116379 | 9/2011 |
| WO | WO 2014/138284 | 9/2014 |
| WO | WO 2014/138482 | 9/2014 |
| WO | WO 2016/040526 | 3/2016 |
| WO | WO 2016/077783 | 5/2016 |
| WO | WO 2017/015632 | 1/2017 |
| WO | WO 2018/140535 | 8/2018 |
| WO | WO 2019/152598 | 8/2019 |
| WO | WO 2022/266022 | 12/2022 |

OTHER PUBLICATIONS

Black MD, M., Division of Pediatric Cardiac Surgery, Standford University School of Medicine, California, USA, Minimally Invasive Pediatric Cardiac Surgery, Online Article in 4 pages.

Ethicon Wound Closure Manual—Chapter 6, Research and Development at Ethicon, Inc.—An Ongoing Process of Change and Improvement, Online at www.ethiconinc.com in 4 pages.

Gersak MD, Ph.D., B., "Mitral Valve Repair or Replacement on the Beating Heart", The Heart Surgery Forum #2000-1989, Jun. 8, 2000, pp. 232-237, 2000 Forum Multimedia Publishing, LLC.

Perclose A-T, 6F Suture-Mediated Closure (SMC) System, Instructions for Use distributed in the U.S. by Abbott laboratories, Inc. 2002, 2006 Abbott Laboratories in 11 pages.

Quealy et al., "Use of Combined Intravascular Ultrasound and PTCA Catheter: Clinical Utility", Chapter 12, pp. 245-250.

International Search Report and Written Opinion issued in PCT Application No. PCT/US2014/021410, dated Jun. 25, 2014, in 15 pages.

International Search Report and Written Opinion issued in PCT Application No. PCT/US2014/020867, dated Jun. 23, 2014, in 22 pages.

International Preliminary Report on Patentability issued in PCT Application No. PCT/US2014/021410, dated Sep. 8, 2015, in 8 pages.

International Preliminary Report on Patentability issued in PCT Application No. PCT/US2014/020867, dated Sep. 8, 2015, in 11 pages.

International Search Report and Written Opinion issued in PCT Application No. PCT/US2015/049251, dated Dec. 29, 2015, in 11 pages.

International Preliminary Report on Patentability issued in International Application No. PCT/US2015/049251, dated Mar. 14, 2017, in 7 pages.

* cited by examiner

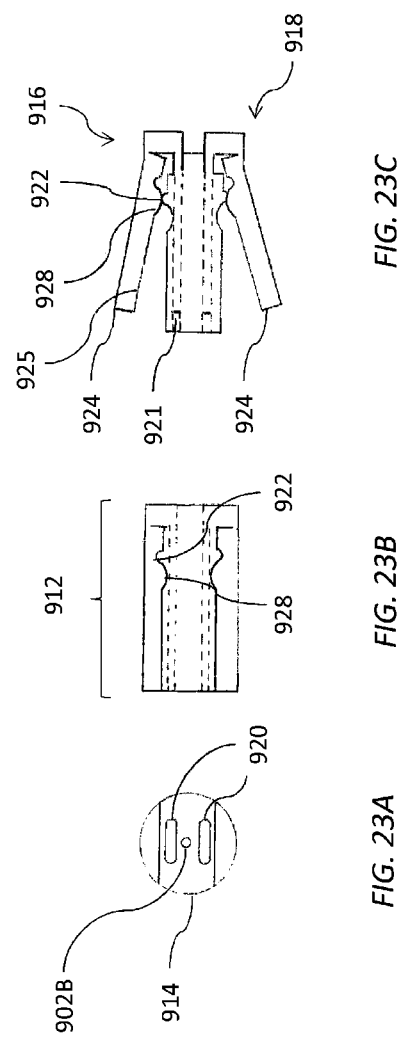

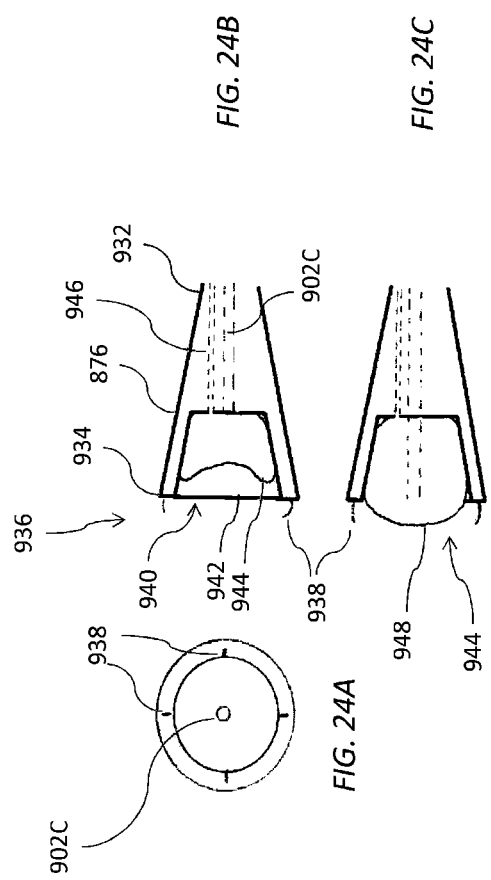

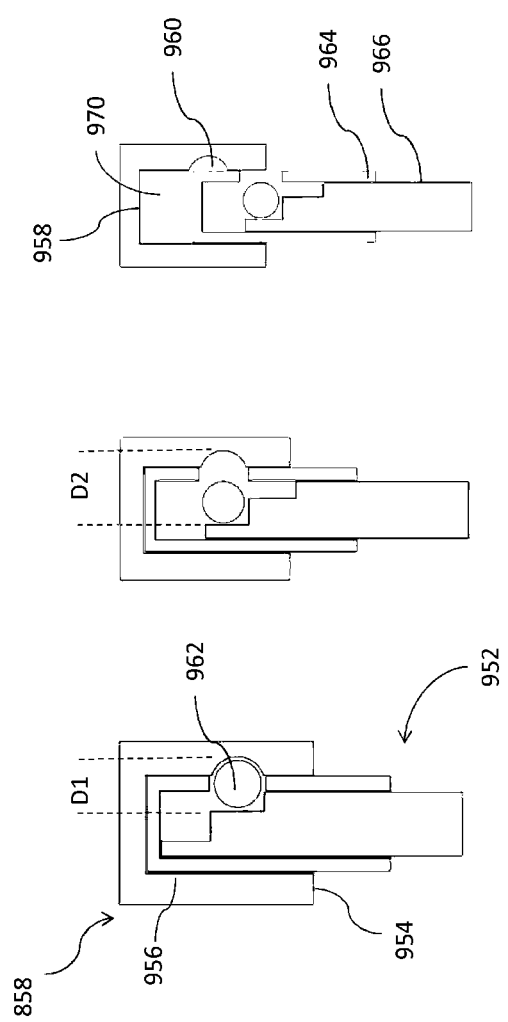

METHOD AND APPARATUS FOR PERCUTANEOUS DELIVERY AND DEPLOYMENT OF A CARDIAC VALVE PROSTHESIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to cardiac valve prostheses and to apparatuses and methods for deploying such devices in a minimally invasive manner.

Description of the Related Art

A major type of heart disease is valvular insufficiency, also called valvular regurgitation, which is characterized by the improper closing of a heart valve. A heart valve consists of a number of leaflets—either two or three—that swing open to allow blood to flow forward (anterograde) out of a heart chamber, and then swing closed to form a tight seal, preventing blood from leaking backwards (retrograde). Valvular insufficiency may result from a variety of problems with the components which make up the valve—for example, the leaflets themselves may degenerate, the tissue cords that tether the leaflets to muscles within the heart may break, or the ring of tissue within which the valve is seated (called the "annulus") may expand after heart attacks or from congestive heart failure. Each of these problems leads to a common element in valvular regurgitation: when closed, the edges of the valve leaflets no longer fit snuggly next to each other and allow retrograde flow.

Mitral regurgitation (MR) (insufficiency of the valve that connects the left atrium with the left ventricle of the heart) and tricuspid regurgitation (TR) (insufficiency of the valve that connects the right atrium with the right ventricle of the heart) contribute significantly to cardiovascular morbidity and mortality. MR is a debilitating disease that can lead to serious complications and possible death. Its symptoms include shortness of breath, rapid respirations, palpitations, chest pain, and coughing. MR leads to heart failure and pulmonary edema and also predisposes patients to other conditions, such as stroke, arterial embolus, and arrhythmias, including atrial fibrillation and lethal ventricular arrhythmias. Detection and timely effective treatment of MR leads to higher survival rates, decreased complications, and increased comfort for patients.

A commercially available method of definitively repairing atrioventricular valvular regurgitation is open-heart surgery. In this procedure, the patient is first anesthetized and then subject to a thoracotomy. Access to the patient's heart is achieved by making a large incision, retracting the skin, muscle, and bony structures. The surgeon must stop the beating of the heart and cut it open to directly visualize the valve. The surgeon then may repair the valve surgically, or remove the valve and implant a prosthetic valve. This requires placing the patient on cardiopulmonary bypass, which involves applying a heart-lung machine to the patient that circulates oxygenated blood throughout the body in place of the working heart and lungs. After the heart is bypassed and is stopped, its structure can be visualized.

Although open-heart surgery is a successful method of repairing or replacing faulty heart valves, it poses a significant risk to the wellbeing of the patient, including death, severe injury, and disability. There is a risk of ischemic or other damage to the heart and other vital organs resulting from the discontinuance of the heart's normal function. The heart-lung machine may also cause abnormalities of the patients circulatory, respiratory, hematologic and neurologic systems. There is a risk of stroke and other consequences from emboli released into the blood during the surgery and during initiation of cardiopulmonary bypass. There is a risk of heart attack. Significant damage occurs to the tissues and bone retracted from the patient's chest while gaining access to the heart. Post-operative complications such as wound infection, pneumonia, and venous thrombosis occur because of the extent of incisions and the patient's debilitated state. Also, cardiopulmonary bypass carries with it a risk of renal insufficiency, particularly in patients with borderline kidney function. Such patients may require dialysis after surgery due to the stress on the kidneys during bypass. Consequently, a patients recovery can be painful, discomforting, long in duration, and costly.

A minimally invasive, beating-heart procedure that would not expose the patient to these risks is therefore desirable. Moreover, a limited surgical approach or percutaneous approach would decrease or eliminate the tissue trauma that occurs from the extensive incisions of open-heart surgery, sparing patients pain, improving recovery time, and decreasing post-operative complications.

A very large population exists that would benefit from an alternative method of valve repair. Approximately 10% of coronary artery bypass surgeries include mitral valve repair or replacement, which amounts to 75,000 to 100,000 of such procedures per year world-wide. In addition, significant MR and/or TR complicate 30-60% of patients with congestive heart failure, contributing to their impaired cardiac function and causing significant morbidity. However, because of the significant risks involved in open-heart surgery, many of the patients are unable to undergo valve repair. Thus, a successful percutaneous or minimally-invasive method of valve repair on the beating heart would have extraordinary clinical benefit.

Commercial products directed to repairing the mitral valve of the human heart with a minimally invasive, beating-heart procedure have significant limitations. Several factors are responsible for this. First, the heart and its associated valves are not directly visualized or accessible. One can use imaging techniques such as fluoroscopy or echocardiography, but these provide a two-dimensional image and a limited field of view. Three-dimensional imaging technologies, including advanced forms of echocardiography, are available but only in a limited number of medical centers and only to very few clinicians trained to use them. Second, it is extremely difficult to immobilize the rapidly moving heart valve leaflets for repair purposes while the heart is beating. Not only are the leaflets moving back and forth rapidly, but also they each have a different shape and geometry. Thus, no single device or methodology has successfully been used to repair heart valves in a minimally invasive manner on a beating heart.

Efforts have been made to commercialize catheter based valve clip devices, though such devices are not yet approved for use in the United States. These devices are delivered by a catheter system percutaneously on a catheter device that is articulated to steer a clip device into place. The catheter system is placed over a guidewire. The device has a dilator that facilitates insertion into the left atrium. Thereafter, the dilator is removed and the clip is advanced at the distal end of an inner portion of the catheter system through an outer portion of the catheter system into the left atrium. The inner portion is adjusted to orient the clip such that the clip points down toward the left ventricle. Once pointed downward, arras of the clip are opened. An innermost portion of the catheter system is then projected from the left atrium into the left ventricle, below the valve leaflets. Thereafter, the clip is retracted and closed to hold the leaflets together to reduce MR.

Although these clip devices can be explained relatively simply, the actual use is not simple. For example, steering and orienting the clip is a delicate operation that requires skill foreign to most cardiologists. The delivery device is relatively large at 24 French. It is heavy and rigid and more analogous to a robotic arm than to generally much more flexible devices regularly used by cardiologists. Because of its rigidity, it is steered using dials that actuate a complex mechanism to orient it in three degrees of freedom. This intricate control system for orienting the rigid arm is only accurately positioned through the use of complex imaging technologies. The rigidity of the system eliminates tactile feedback to the doctor and thus imaging is the only means for achieving and/or confirming placement.

While technically able to repair a mitral valve through peripheral access, these devices and the procedures in which they are used still are very costly to the patient and to the health care system in general. While these clips devices are described as being able to release, re-approach, and recapture the leaflets, such re-working procedures increase the overall procedure time which is disadvantageous for the patient and the physician. For example, the MitraClip procedure is indicated as taking 2 to 4 hours, which is comparable to open heart valve repair surgery. In practice, the procedure can take two to three times longer than this due to poor initial placement, release and re-grasping efforts. Also, the patient must be under general anesthesia, and both an interventional cardiologist and an echo cardiologist must be present during the procedure. These and other aspects of the MitraClip design discussed in the EU Heart Journal article of May 23, 2011 make it inconvenient and costly to use.

SUMMARY OF THE INVENTION

Disclosed herein is a method of performing a procedure in the heart. In the method, a catheter is provided that has an elongate flexible body, a proximal end, and a distal end. The catheter also has a procedure zone spaced proximally apart from the distal end. The proximal and distal ends are separable from, at or adjacent to the procedure zone. The catheter can be advanced antegrade through the mitral valve and through the aortic valve and into the aorta. When so advanced, the procedure zone is positioned upstream from the aortic valve. A procedure is performed from the procedure zone. At least one of the proximal portion and the distal portion are separated from, at or adjacent to the procedure zone. The proximal and distal portions of the catheter are separately removed from the patient. Separately removing of the proximal and distal portions can follow activating a low profile detachment actuator from the proximal and/or distal ends of the catheter.

In another embodiment, a method of orienting a first and second tissue grasper with respect to the mitral valve is provided. The method includes providing a catheter having an elongate, flexible body, with a proximal end, a distal end and first and second tissue graspers spaced apart from the distal end. The distal end of the catheter is transluminally advanced from the left atrium through the mitral valve and along the left ventricular outflow tract into the ascending aorta. Such advancement positions the first and second tissue graspers adjacent a central zone of the mitral valve. Fine adjustment of the graspers can then be performed by actuating a steering device at the proximal or distal end of a catheter body. Thereafter, the distal end of the catheter is drawn out of a peripheral artery.

In another embodiment, a method of repairing a mitral valve is provided. The method includes providing a catheter body or system having an elongate, flexible body, with a proximal end and a distal end. The distal end is transluminally advanced from the left atrium through the mitral valve and along the left ventricular outflow tract into the ascending aorta. A valve repair device is deployed to permanently connect leaflets at a mid-section of a mitral valve while permitting medial and lateral portions of the natural leaflets to open and close. The valve repair device can be actuated by axially displacing one or both of first and second graspers relative to a base portion of the valve repair device to cause one or both of first and second graspers to be laterally displaced from the base portion. The valve repair device can be detached from the distal and/or proximal ends of a catheter body or system.

In another embodiment, a system is provided for performing a procedure in the heart. The system includes a catheter having an elongate flexible body, a proximal end, a distal end, and a procedure zone. The procedure zone is spaced proximally apart from the distal end. Proximal and distal portion of the catheter are separable from the procedure zone. In certain embodiments, the catheter is advanceable antegrade through the mitral valve. That is, the elongate body can have a length to extend from a peripheral venous site to the heart, into the atria of the heart, and through the mitral valve. The elongate body further can have a length to extend from a peripheral venous site through the heart and aortic valve and into the aorta. The elongate body further can have a length to extend from a peripheral venous site through the heart such that the procedure zone is positioned upstream from the aortic valve. The procedure zone can be configured to perform a procedure in the heart. The proximal portion can be separable from the distal portion from, at or adjacent to the procedure zone. The elongate flexible body of the catheter can be configured such that a distal portion of the catheter can extend to a peripheral arterial site, e.g., when the proximal portion is disposed from the heart to a peripheral venous site. The distal portion is configured to be separated from the procedure zone by actuating a low profile device, such as a device disposed through a distal catheter body and at the arterial access site when in use such that the distal catheter body can be removed from the arterial site. The proximal portion can be removed from the peripheral venous site following actuating a low profile device disposed at least partially through a proximal catheter body and at the venous access site when in use.

In another embodiment, a system is provided for orienting first and second tissue graspers of a heart prosthesis with respect to the mitral valve. The system includes a catheter having an elongate, flexible body, with a proximal end and a distal end. First and second tissue graspers are provided in the system spaced apart from the distal end of the elongate flexible body. The tissue graspers can be actuated by control surfaces or interfaces disposed on an inwardly facing surface of the graspers. The catheter is configured to be advanceable from a peripheral venous site to the left atrium and through the mitral valve and into the ascending aorta (e.g., along the left ventricular outflow tract). The catheter is configured to position the first and second tissue graspers adjacent to a central zone of the mitral valve. A distal portion of the catheter is configured to be disposed in a peripheral artery and through a percutaneous access site while the graspers are adjacent to the central zone such that a distal portion of the catheter can be drawn out of the peripheral artery.

In another embodiment, a mitral valve repair apparatus is provided that includes a catheter having an elongate, flexible body. The body can have a proximal end and a distal end. A distal portion, e.g., the distal end, of the body is advanceable from the left atrium through the mitral valve and along the left ventricular outflow tract into the ascending aorta. The elongate, flexible body can be configured to reach the heart from a femoral venous or other peripheral venous site. The apparatus also includes a valve repair device configured to permanently connect leaflets at a mid-section of a mitral valve while permitting medial and lateral portions of the natural leaflets to open and close. The valve repair device includes leaflet graspers that can be independently actuated by a force generated or transmitted through the catheter, e.g., by fluid pressure in a control lumen. The graspers can include clip faces that can be opened and held open by other devices, including any one or a combination of positive displacement pistons, force derived from remotely applied torque or tensile force, cam-type profiles shaped into the grasper or clip body. The valve repair device is detachably coupled with the distal and proximal ends of the catheter.

In another embodiment, a system is provided for deploying a mitral repair device. The system includes an elongate catheter body, an implantable mitral prosthesis, and a control device. The elongate catheter body is sized to extend from a peripheral venous site, through the heart, to a peripheral arterial site. The implantable mitral prosthesis is disposed between a proximal catheter portion and a distal catheter portion of the elongate catheter body. The proximal catheter portion can be a venous portion in that at least a portion thereof is disposed in the venous vasculature during a procedure. The distal catheter portion can be an arterial portion in that at least a portion thereof is disposed in the arterial vasculature during a procedure. In some variations, the control device is disposed in the proximal or venous portion of the elongate catheter body to facilitate control of the prostheses or system.

In some variations, the control device provides fine adjustment in the position or orientation of the prostheses and is controlled from the venous and/or the arterial end. For example, the implantable mitral prosthesis can be initially positioned and/or oriented at the mitral valve site by manipulation of one or both of the venous portion and the arterial portion. The implantable mitral prosthesis can be moved from the initial position by actuating the control device from the venous and/or arterial end to change the location of the prosthesis along or to change the orientation of the prosthesis relative to a cardiac structure, such as the line of coaptation of the mitral valve.

In some variations, the control device provides for low profile detachment of proximal or distal catheter portions of the system. For example, the control device can be actuated to cause two portions of the system that are coupled together to become de-coupled. This can facilitate low profile delivery of and subsequent detachment of a prosthesis from other portions of the system.

In some variations, the control device provides for actuating of, e.g., inflation and deflation of, a dilator structure. A dilator structure can be in the form of a conical or otherwise tapered portion with a proximally expanding profile.

Various embodiments are also directed to a mitral valve prosthesis. The prosthesis includes an elongate arcuate body, a base, and arcuate anterior and posterior leaflet grasping elements. The elongate arcuate body has a proximal end and a distal end. The base is disposed between the proximal and distal ends of the elongate body. The arcuate anterior leaflet grasping element is coupled with the base, e.g., slidably engaged with or articulated at or adjacent to the distal end of the elongate body. The arcuate anterior leaflet grasping element is movable between an open position and a closed position, e.g., upon sliding motion along a control interface. The arcuate posterior leaflet grasping element is coupled with the base at or adjacent to the distal end of the elongate body. The arcuate posterior leaflet grasping element is movable between an open position and a closed position.

In certain embodiments of the mitral valve prosthesis, when the posterior leaflet grasping element is in the closed position, the posterior leaflet grasping element is received in a space at least partially bounded by the base.

In certain embodiments of the mitral valve prosthesis, a flush surface is provided between the base and side surfaces of at least one of the anterior and poster leaflet grasping elements.

In certain embodiments of the mitral valve prosthesis, a lumen and a fluid actuator (e.g., hydraulic, pneumatic, etc.) are disposed in the base for actuating at least one of the anterior and poster leaflet grasping elements.

In certain embodiments of the mitral valve prosthesis, a first lumen and a first fluid actuator is disposed in the base for actuating the anterior leaflet grasping element and a second lumen and a second fluid actuator is disposed in the base for actuating the posterior leaflet grasping element.

In certain embodiments of the mitral valve prosthesis, an indexing feature is disposed on a proximal portion of the prosthesis for providing a selected rotational position of the prosthesis relative to a catheter body.

In certain embodiments of the mitral valve prosthesis, a control member channel is disposed on a proximal face of the base for engaging a guidewire or push clement.

In certain embodiments of the mitral valve prosthesis, a retention member is provided that is configured to be advanced over a side surface of the arcuate body to a position around at least one of the anterior and posterior leaflet grasping elements to hold the grasping element against the base.

In certain embodiments of the mitral valve prosthesis, a bight is formed or provided between the base and at least one the anterior and posterior grasping elements, e.g., when one or both of the anterior and posterior leaflet grasping element is in the open position. The bight is proximally facing, e.g., when having a larger transverse dimension adjacent to the proximal end of the prosthesis than adjacent to the distal end thereof.

In certain embodiments of the mitral valve prosthesis, a hinge is provided between at least one of [a] the base and a distal portion of the anterior leaflet grasping element and [b] the base and a distal portion of the posterior leaflet grasping element.

In certain embodiments of the mitral valve prosthesis, a spring is coupled with a first portion of the posterior leaflet grasping element and an actuator coupled with a second portion of the posterior leaflet grasping element, the hinge being disposed between the first and second portions.

In a further variation, a mitral valve prosthesis includes an elongate arcuate body that has a proximal end and a distal end. The prosthesis also has a base, a first leaflet grasping element, and a second leaflet grasping element. The base is disposed between the proximal and distal ends of the elongate body. The first leaflet grasping element can be an anterior grasping element and the second leaflet grasping element can be a posterior grasping element. At least one of the first and second leaflet grasping elements can have an arcuate configuration, e.g., an arcuate surface as viewed in transverse cross-section. The first leaflet grasping element can be moveably coupled to the base adjacent the distal end of the elongate body. The first leaflet grasping element can be movable between an open position and a closed position. The second leaflet grasping element can be moveably coupled to the base adjacent to the distal end of the elongate body. The second leaflet grasping element can be movable between an open position and a closed position. The prostheses can have a control surface disposed on the base and interacting with one of the first and second leaflet grasping elements to open the anterior or posterior leaflet grasping elements. The control surface can be disposed between the first and second leaflet grasping elements when the prostheses is in a closed configuration.

The control surface can include a plurality of undulating profiles. One of the undulating profiles can be disposed on the base and one can be disposed on a grasping element. The undulating profiles are arranged to be generally in-phase in a configuration in which the grasping element is closed and generally out-of-phase when the grasping element is open. The out-of-phase configuration can provide for axial alignment of peaks of opposed profiles. The in-phase configuration can provide for axial alignment of peaks of one profile with valleys of another profile. As used herein, in-phase and out-of-phase can include but are not limited to require regular undulations, and can include an axial surface with any type of varying lateral extent.

BRIEF DESCRIPTION OF THE DRAWINGS

FIGS. 23A-23C illustrate additional embodiments of mitral valve prostheses.

FIGS. 24A-25C illustrate detachment actuators to assist in separating various embodiments of mitral prostheses from delivery systems disclosed herein.

DETAILED DESCRIPTION OF THE PREFERRED EMBODIMENT

Figure 1:
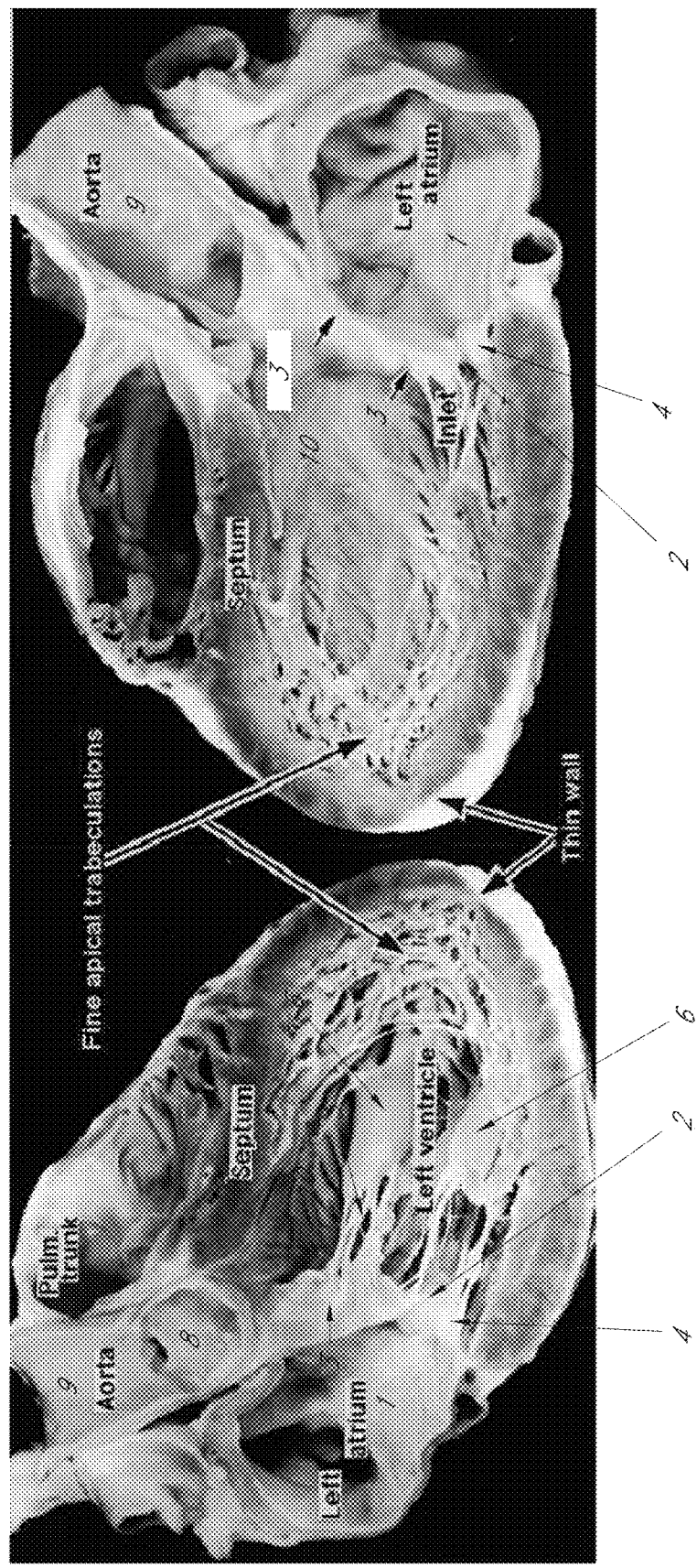
FIG. 1 is a photograph of a pathologic specimen of a human heart sectioned along its long axis, demonstrating the pertinent anatomical structures and landmarks important to device operation.

In FIG. 1, a longitudinal section of the human heart is shown demonstrating the left atrium 1, the mitral valve orifice 2, the anterior leaflet 3 of the mitral valve, and the posterior leaflet 4 of the mitral valve. The subvalvular apparatus consists of the numerous chordae tendinae 5 and the papillary muscles 6. The left ventricular outflow tract (LVOT) 10 is a channel formed by the anterior leaflet 3 of the mitral valve and the interventricular septum.

Figure 2:
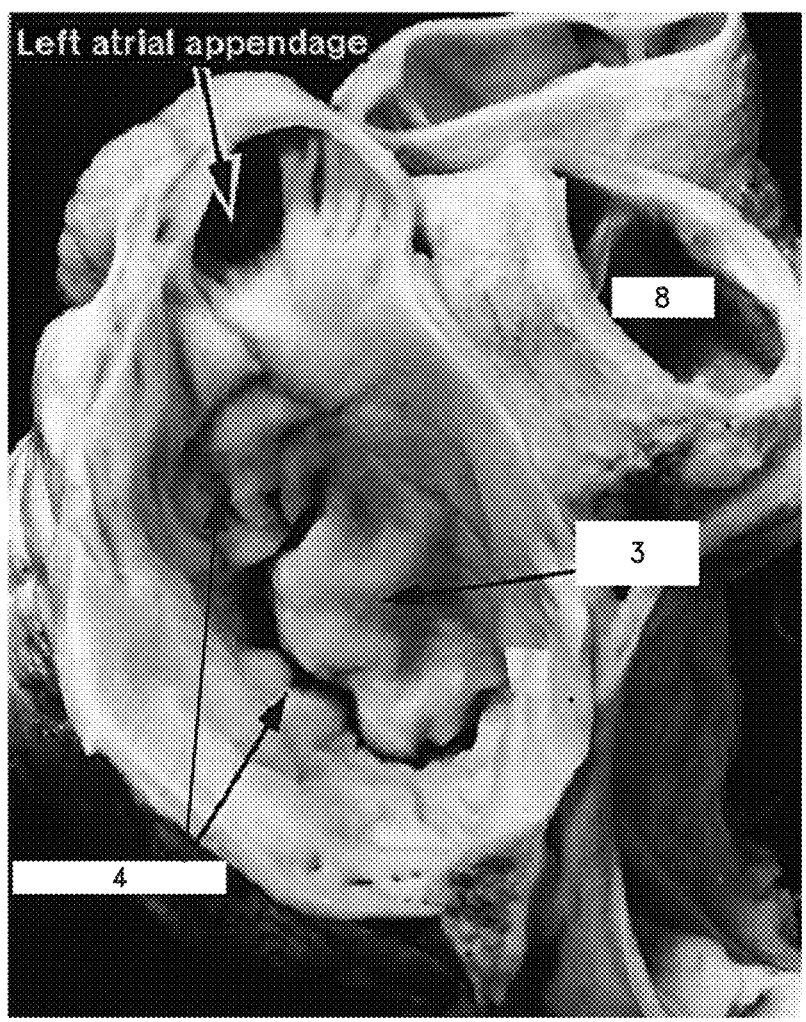
FIG. 2 is a photograph of a pathologic specimen of a human heart, sectioned in short axis at the level of the left atrium, demonstrating the anatomy of the mitral valve leaflets as viewed from the perspective of the left atrium and the approach according to certain embodiments of the invention.
Figure 2A:
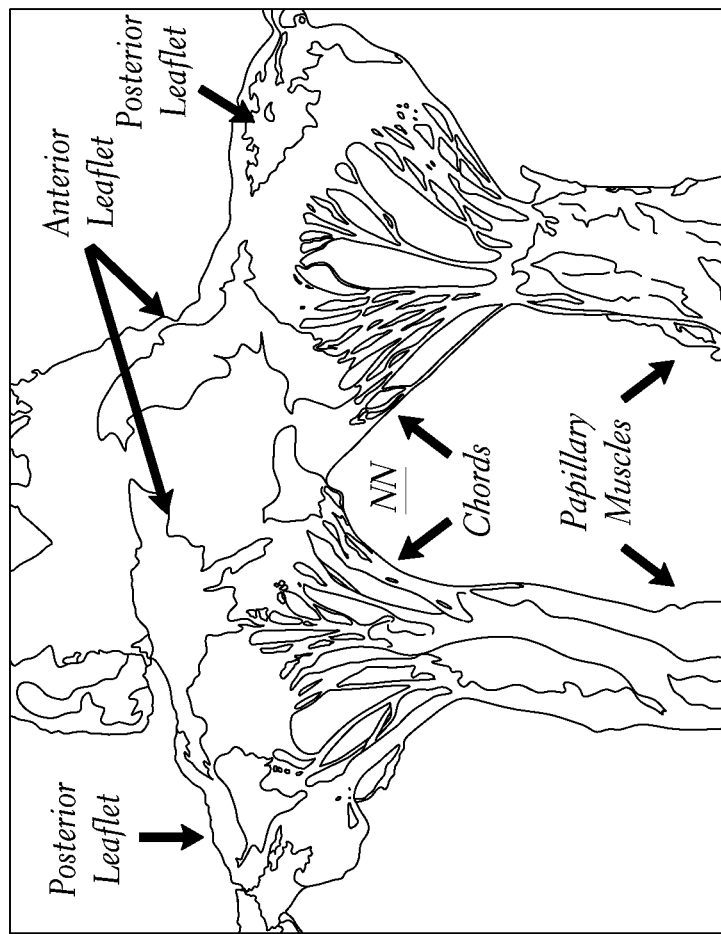
FIG. 2A is a photograph of a partial dissection of a mitral valve showing the sub-valvular apparatus in greater detail.

In FIG. 2, a short axis view of the mitral valve is seen at the level of the left atrium. This demonstrates the asymmetric nature of the mitral valve leaflets. The posterior leaflet 4 has a broad base and of narrow width, while the anterior leaflet 3 has a relatively narrow base and a substantial width. FIG. 2A is a partial dissection of the mitral valve further illustrating the sub-valvular apparatus. These figures illustrate the trajectory along which a catheter device is advanced according to this disclosure to position a valve repair device. As discussed in greater detail below, the trajectory is from the left atrium 1, through the mitral valve orifice 2, between the papillary muscles 6, through the LVOT 10, across the aortic valve 8 and into the ascending aorta 9.

With particular reference to FIG. 2A, when properly positioned, the path will be centered between the posterior-most chord of the anterior portion of the sub-valvular apparatus and the anterior-most chord of the posterior portion of the sub-valvular apparatus. The superior aspects of these chordae extend toward one another, forming an anatomical narrows that is exploited by the methods and apparatuses herein for rapid positioning of a valve repair device. As discussed in greater detail below a trajectory extending from a wall of the aorta, through this narrows region and up through the mitral valve into the left atrium will roughly bisect the mitral valve in the medial-lateral direction. Thus, the methods and devices herein are less dependent upon difficult to interpret imaging technologies and the need to position and reposition a valve repair device to get a good result, e.g., significantly reducing MR.

1. Orienting a Valve Repair Device

FIGS. 3-9 illustrate methods for deploying a valve repair device. In these techniques, the valve repair device is a durable device and can be an apposing element, a fastening device, or a fastener that reduces MR. The valve repair device preferably is deployed to secure together a medial-lateral central zone of the valve to create a double orifice at the mitral valve. The valve repair device is configured to minimize a chance of leaflet tear, such as by grasping a sufficient area of the valve to reduce concentration of force, as discussed further below. FIGS. 16-20 illustrate an embodiment of a valve repair device that enhances coaptation compared to other mitral valve prostheses as discussed below and a system and method for deploying the valve repair device.

Figure 3:
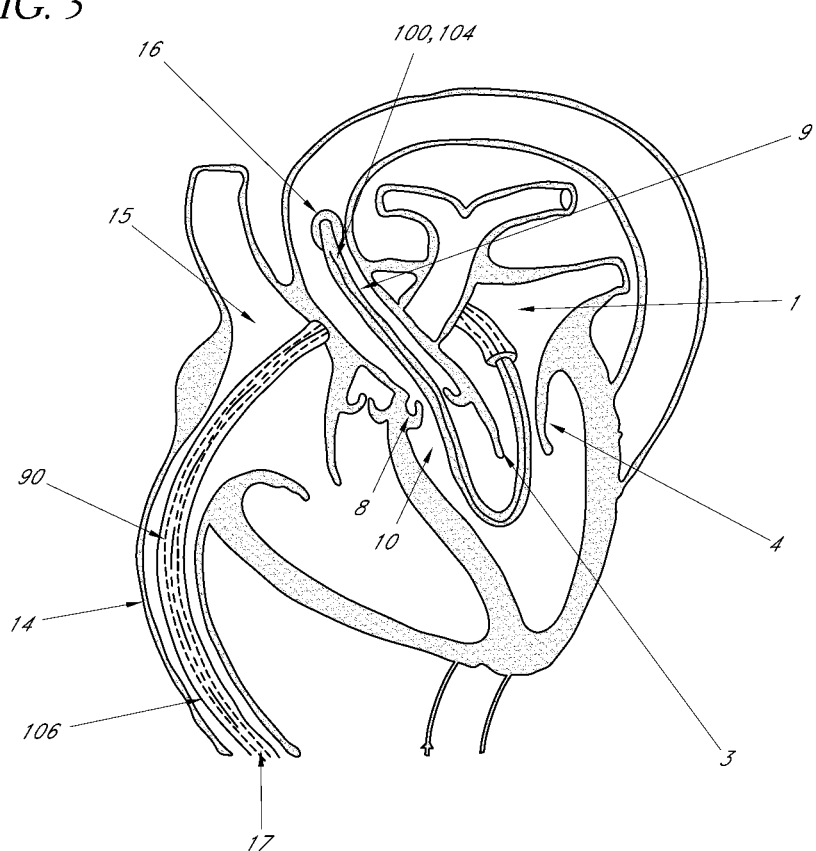
FIG. 3 is a schematic representation of a human heart and one embodiment of the present invention showing the position within the heart and blood vessels that provides correct orientation, the proximal end being accessible at a first peripheral venous location.

FIG. 3 shows the body of a catheter 100 with a distal portion 104 disposed in the heart and the ascending portion of the aorta 9. A method for delivering the catheter 100 to this position can include accessing a peripheral vein and providing access to the left atrium 1 through the atrial septum, e.g., by opening and/or enlarging the fossa ovalis. Standard transseptal access devices can be advanced into a femoral vein and through the inferior vena cava 14 to cross the atrial septum. In one embodiment a sheath 90 is advanced across the septum and into the left atrium. After access is provided, the catheter 100 can be advanced into the left atrium 1 and through the mitral valve between the anterior and posterior leaflets 3, 4. The catheter 100 can be further advanced into the LVOT 10 and into the aorta 9 in the position shown in FIG. 3. A proximal portion 106 of the catheter 100 extends proximally from the heart, e.g., through the sheath 90, and exits the body at a peripheral venous location, such as a femoral vein.

Figure 4:
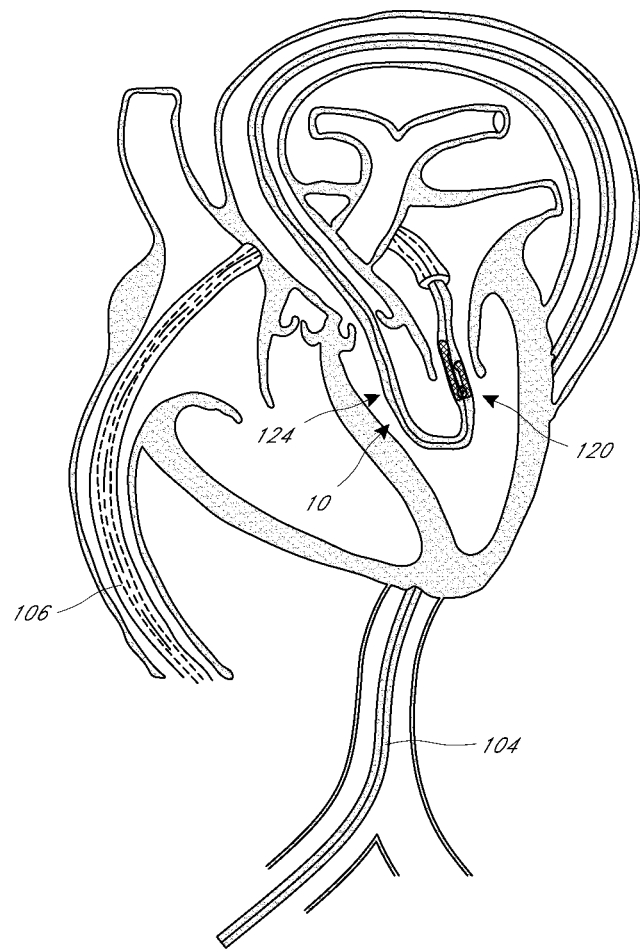
FIG. 4 is a schematic representation of a human heart and one embodiment of the present invention showing a distal portion of a catheter device advanced toward a femoral artery for accessing the distal portion.
Figure 10:
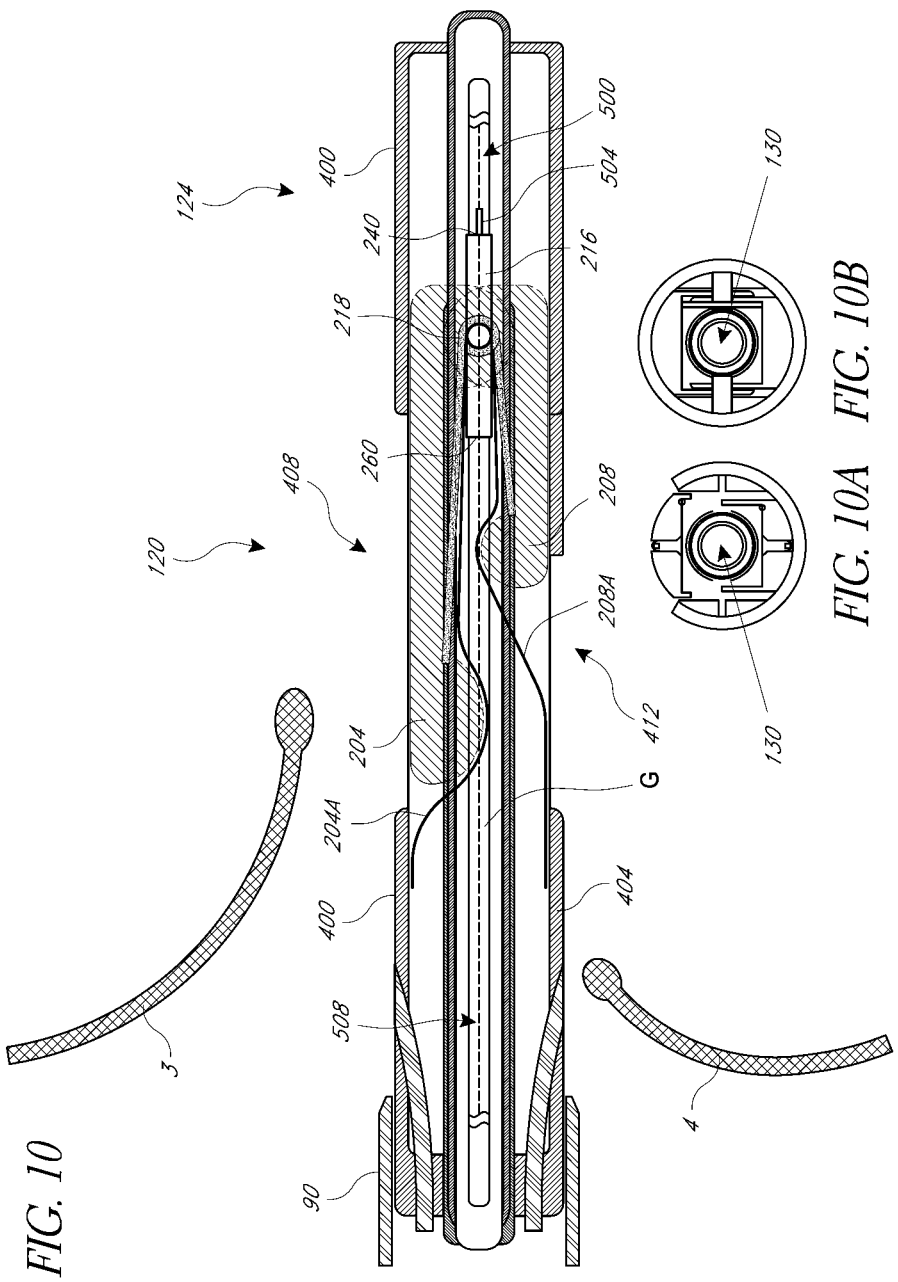
FIGS. 10-15 illustrate aspects of valve repair devices with pairs of arms configured to capture valve leaflets and their deployment at a valve.

FIG. 4 shows a later step in which the distal portion 104 of the catheter 100 is advanced over the arch of the aorta 9 and further toward a peripheral artery. FIG. 10 shows that a lumen 130 can be provided in the catheter 100. The lumen 130 can be sized to receive a guidewire for positioning the catheter 100. In some embodiments as discussed below, the lumen 130 can be used to deploy and operate an imaging device at least in an area within or adjacent to the heart, e.g., in a procedure zone. Advancing the catheter 100 in this manner can be accomplished by any standard technique, such as tracking a previously placed guidewire or a flow directed catheter. Access can be provided to the peripheral arterial site by conventional means. A snare or other grasping device can be used to draw the distal end of a guidewire or other tracking device out of the patient such that a continuous guiding track or circuit from peripheral venous access to peripheral arterial access is provided. The peripheral femoral venous access is a first access site and the femoral (or other peripheral) arterial access is a second access site, and the first and second access sites can be accessed simultaneous as discussed below.

In another embodiment, guiding devices such as guidewires are not used to deliver the distal portion 104 to the peripheral arterial site from the heart. Instead, the catheter 100 is directed unguided or retracted toward the vicinity of the second access site without a guidewire. A balloon or highly flexible distal region can be a useful structure for unguided delivery to a peripheral arterial site. A snare may then be used to capture the distal end of the distal portion 104. Either tracking a guiding device or by use of the snare, the distal end of the distal portion 104 of the catheter 100 can be directed or drawn out of the body at the peripheral arterial access site.

Figure 3A:
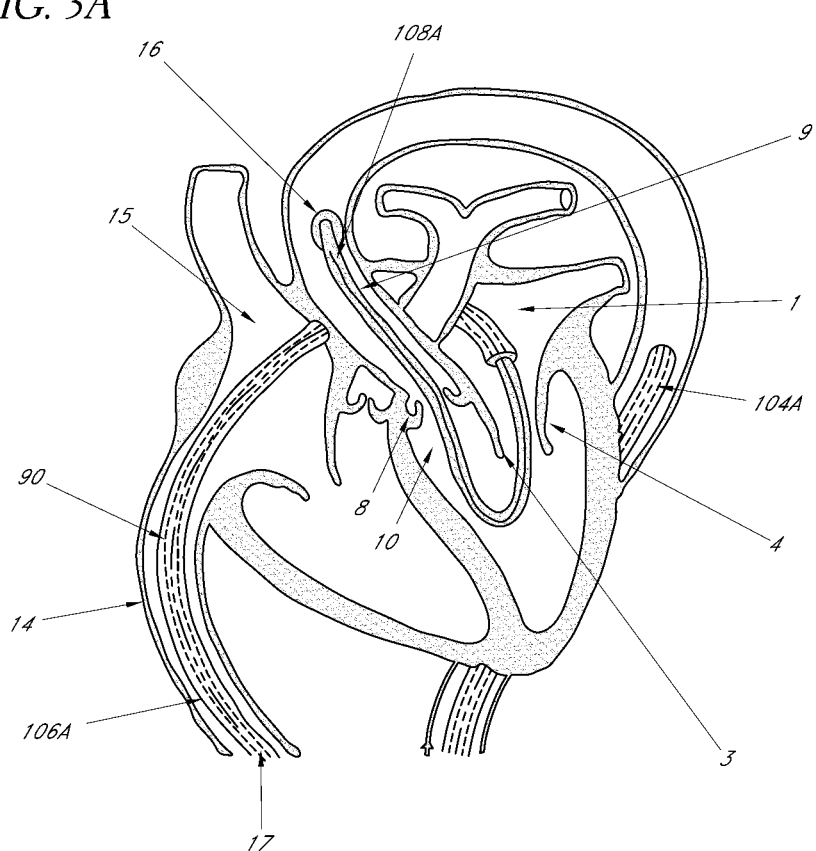
FIG. 3A illustrates part of a venous-arterial rail method that can be combined with the methods and apparatuses disclosed herein

FIG. 3A shows an alternative approach in which a distal end 108A of the proximal portion 106A can be position through the venous vasculature, across the mitral and aortic valves into the ascending aorta. A capture device 104A can be advanced from an arterial access site up the aorta and into vicinity of the distal end 108A of the proximal portion 106A. The capture device 104A can include a snare or other device to grasp the distal end 108A. In certain embodiments, the capturing device 104A is low profile such that it can engage the distal end 108A and form an outer surface that permits advancement of catheter bodies against flow from the arterial access site to the heart over the capture device 104A. This variation is discussed more in connection with FIG. 20.

Figure 4A:
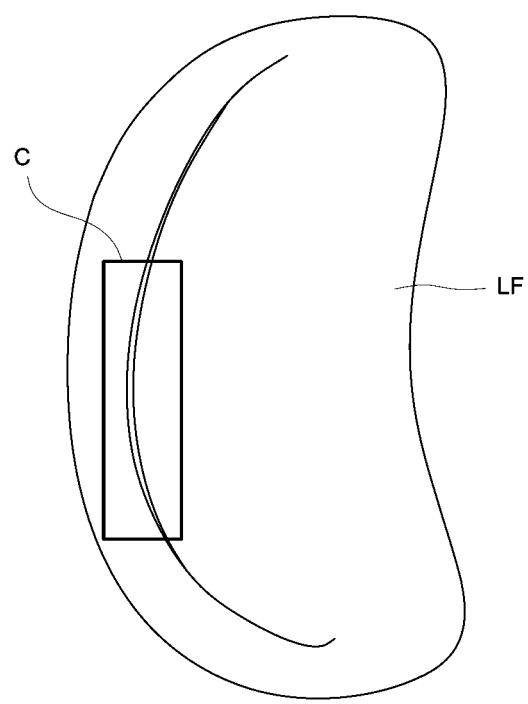
FIG. 4A is a schematic of a mitral valve showing placement of a procedure zone of a catheter device by interaction of an anchor zone with adjacent anatomy.

FIGS. 4 and 10 show that the catheter 100 has a procedure zone 120 and an anchor zone 124. The procedure zone 120 includes one or more devices for interacting with the vessel or a heart valve and/or deploying a valve repair device. The anchor zone 124 is configured to provide fast, consistent and accurate placement of the procedure zone 120 at the correct location along the valve. The positioning is better understood with reference to FIGS. 2A and 4A. As noted above in connection with FIG. 2A, an opening is defined in the sub-valvular apparatus between anterior papillary muscles and posterior papillary leading toward the LVOT 10. The distal portion 104 and anchor zone 120 passes through this opening as the catheter 100 is advanced to the position of FIG. 4. The anchor zone 124 is configured to engage the anatomy distal the mitral valve and to define a predictable, appropriate trajectory through the intervening anatomy and within the mitral valve. As the catheter 100 is placed, the procedure zone 120 follows a trajectory that intersects roughly the medial-lateral central zone of the mitral valve. In FIG. 4A, a box is drawn over a location of the zone C where the procedure zone 120 crosses the mitral valve when the anchor zone 124 engages distal anatomy and the proximal portion 106 of the catheter 100 is disposed proximally through the atrial septum. Because the procedures zone 120 naturally comes to rest at this location, subsequent manipulation is relatively minimal. This permits relatively simple manipulations to orient the procedure zone 120.

Further, to an extent interaction of the catheter 100 with central chordae tendinae can provide a guiding function to proper pre-positioning of the catheter 100. FIG. 2A shows that the posterior most of the chordae tendinae extending from the anterior papillary muscle and the anterior most of the chordae tendinae extending from the posterior papillary muscle further define the opening from the mitral valve to the LVOT 10 and to the aorta. A notch or narrows NN is defined where these chordae tendinae connect to the valve apparatus. When placed as in FIG. 4, the body of the catheter 100 comes to rest in this notch NN and as a result is in or very close to the zone C illustrated in FIG. 4A. Once advanced through the valve and into an anchoring connection with the anatomy, the proximal portion 106 of the catheter 100 can be subjected to a clockwise or counter-clockwise torque to orient the catheter body about its axis but still generally at the zone of coaptation of the leaflets. In other embodiments, a steerable wire can be used to allow anteflection, retroflection or other useful positioning maneuvers of the procedure zone 120. While the catheter 100 generally will place the procedure zone 120 in the area C illustrated in FIG. 4A, these subtle movements can optimize placement within that are, for example centering the procedure zone there.

This anchoring capability of the distal portion 104 of the catheter 100 provides for quicker and more efficient patient care. Other systems dispose a valve clip at the distal-most end of the delivery system and that rely on substantially free hand or proximal end only positioning of the valve in three dimensional space to approach the leaflets in reliance on sophisticated imaging. Although many procedures benefit from sophisticated imaging, and more maneuverability can be useful, free-hand or proximal end only placement of a clip requires too much manipulation to be conveniently and efficiently performed. Greater maneuverability carries with it the substantial chance of misplacement. Therefore, such devices are greatly complicated with features that enable the device to be un-clipped and re-clipped multiple times.

FIGS. 5-9 illustrate the ease of delivery of a valve repair device 200 using the catheter 100 placed as discussed above. The device 200 is advanced through the mitral valve between the leaflets 3, 4 into the left ventricle as the distal portion 104 of the catheter 100 is advanced through the second access site. In one embodiment, the valve repair device 200 is on, is part of, or comprises the procedure zone 120. In this context "valve repair device" is a broad term that includes any device or technique by which MR is reduced while still using the native valve leaflets to provide a valve function, including where the valve function is converted from a single orifice to a double orifice. This term also includes the mitral repair device of FIGS. 16-19 discussed in greater detail below. In one approach, the valve repair device 200 has an anterior element 204 and a posterior element 208. The anterior and posterior elements 204, 208 are configured to engage and secure the anterior and posterior leaflets 3, 4 respectively. Preferably the anterior and posterior elements 204, 208 are adapted to gather portions of the anterior and posterior leaflets 3, 4 and secure them against or within another portion of the valve repair device 200. Examples of structures that can be incorporated into the anterior and posterior elements 204, 208 are discussed in U.S. Pat. No. 6,752,813 to Goldfarb et al.; U.S. Pat. Nos. 7,635,329; and 7,604,646, all which is hereby incorporated by reference herein for this and any other purpose.

Figure 5:
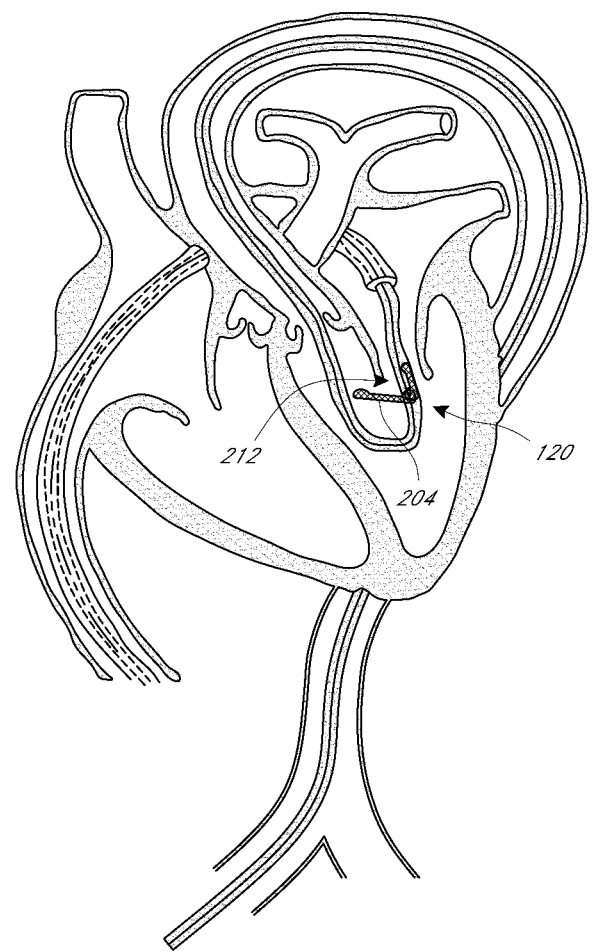
FIG. 5 is an image similar to that of FIG. 4, showing deployment of a valve treatment device.
Figure 6:
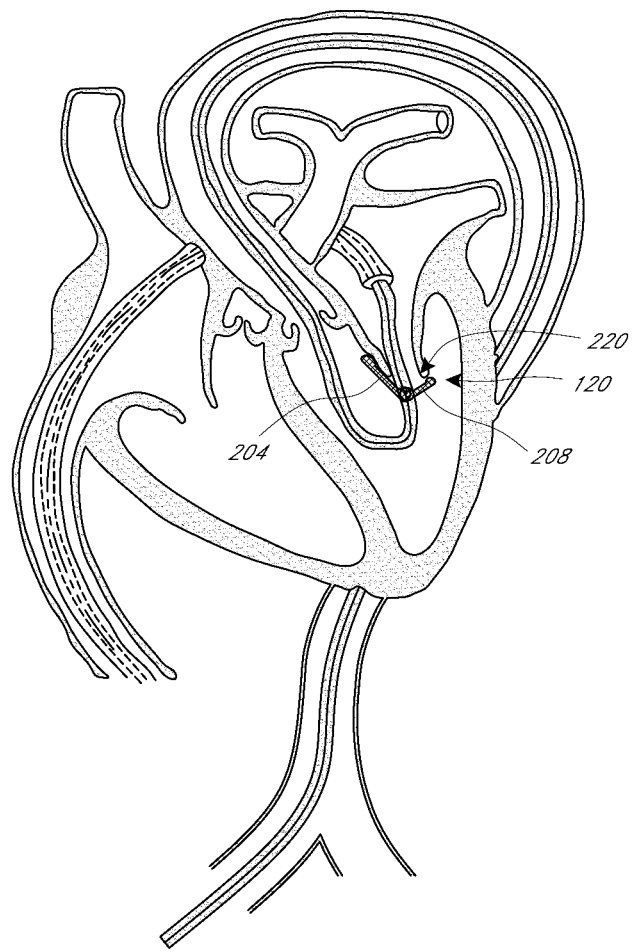
FIG. 6 is an image similar to that of FIG. 4, showing further deployment of a valve treatment device.
Figure 11:
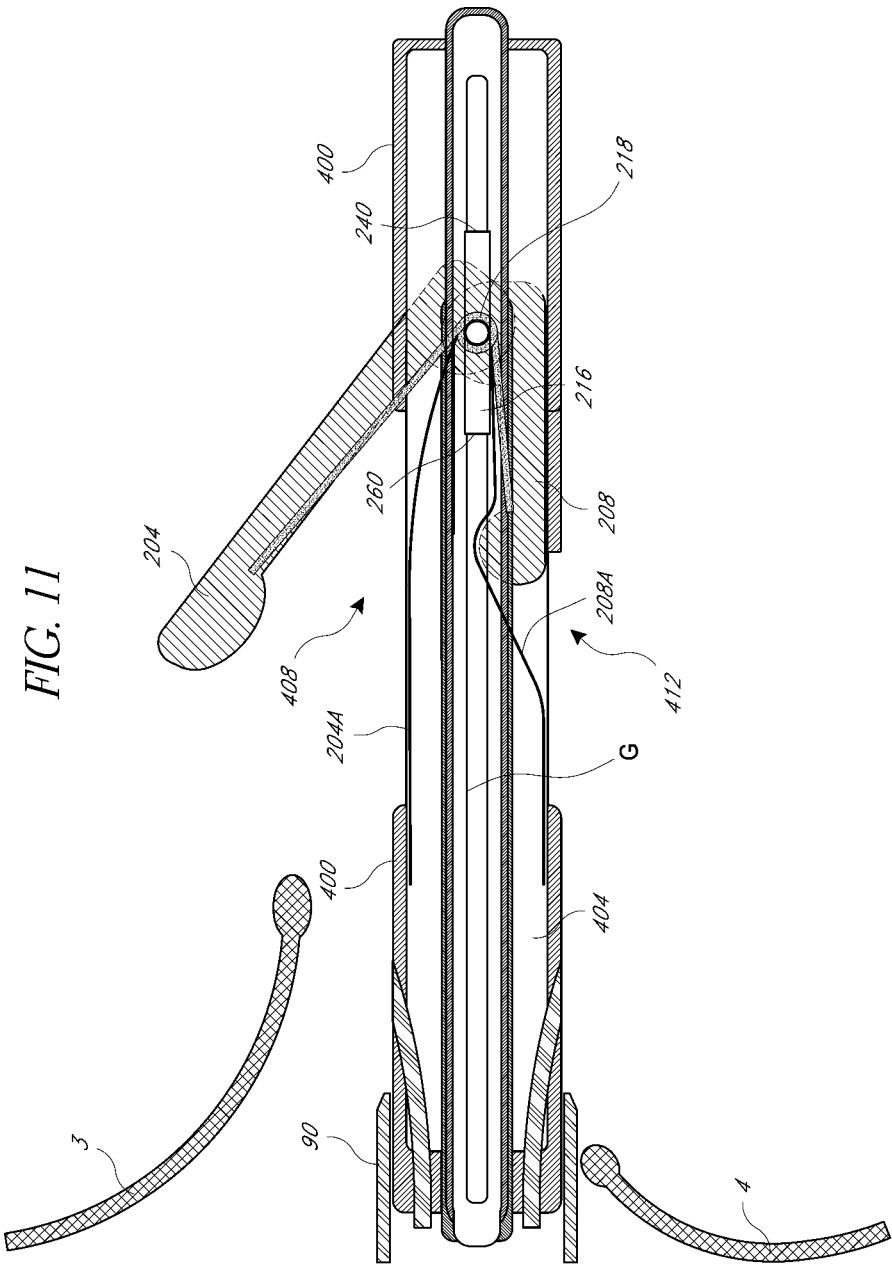

FIGS. 5 and 6 show one technique for capturing the leaflets. As discussed above, this procedure generally is to be performed on a beating heart, in which the mitral valve leaflets 3, 4 are moving rapidly relative to the procedure zone 120. FIGS. 5 and 11 show that the anterior element 204 can be deployed to create a proximally oriented channel or bight 212 between the element 204 and a central hub 216 of the device 200 that is suitable for receiving the valve therein. After the anterior element 204 is deployed slight proximal movement of the catheter 100 causes the leaflet 3 to be disposed in the bight 212. Although the valve is still moving as the heart beats, the anterior leaflet 3 is disposed in or through the bight 212 and remains temporarily gathered. In other words, although the mitral valve is operating and the anterior element 204 is open, the leaflet 3 remains in the bight 212.

Figure 13:
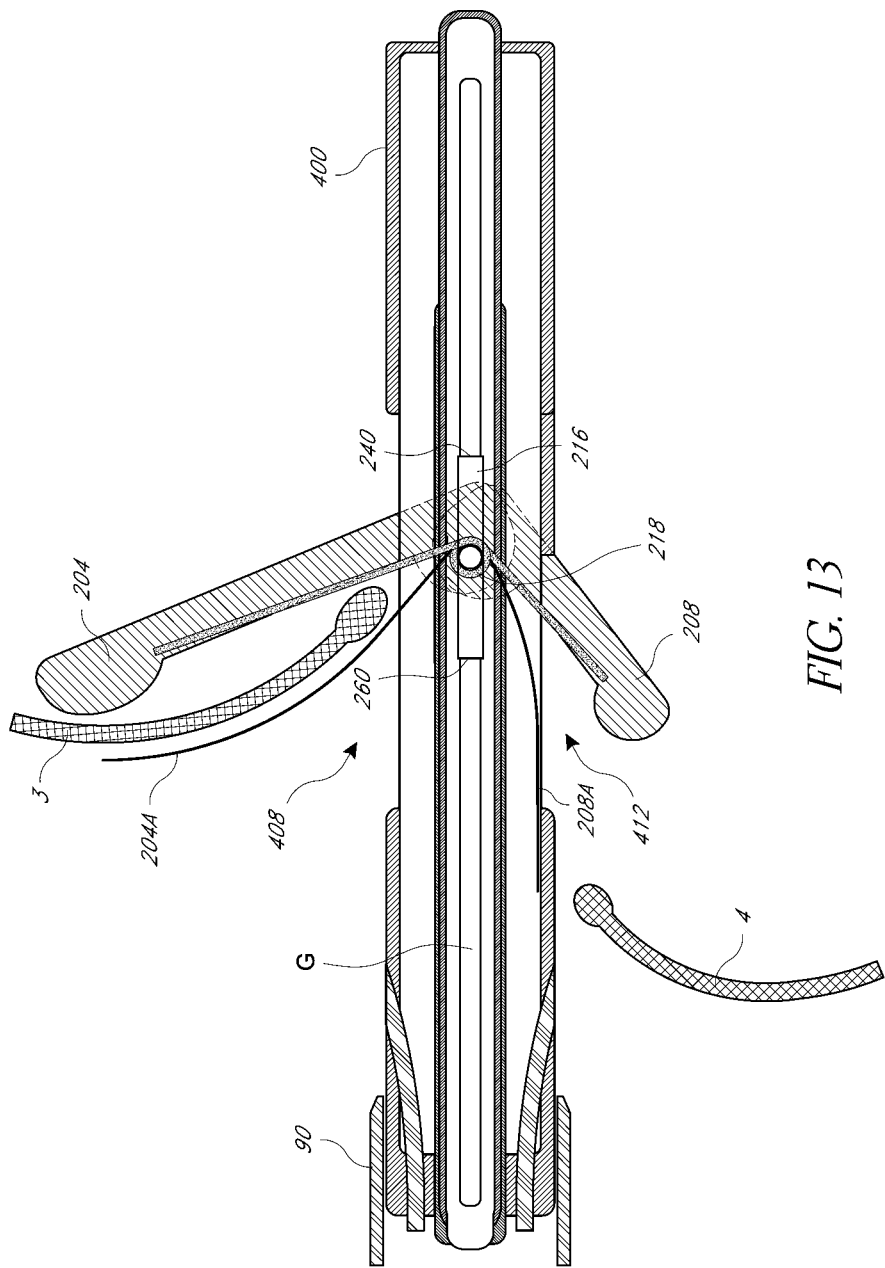

Thereafter, the posterior element 208 is deployed exposing a bight 220 between the element 208 and the hub 216. FIGS. 5 and 13 show the bight 220 in more detail. Slight proximal movement of the catheter 100 causes the leaflet 4 to be disposed in the bight 220. In certain embodiments, suction or a grasper device can be deployed from the catheter to maintain the leaflet in the bight 212, 220, as discussed in U.S. Pat. No. 7,635,329, which is incorporated by reference herein in its entirety and for this purpose. The Appendix includes this patent as part of this application.

The slight proximal movement to position the leaflets 3, 4 in the bights 212, 220 may be preceded with some manipulation of the catheter 100. The manipulation will cause the anterior and posterior elements 204, 206 to be deployed. For example, as discussed in connection with FIGS. 10-14 below the catheter 100 can have a plurality of windows that perm it egress of the anterior and posterior elements 204, 208 for capturing the leaflets 3, 4 respectively. In some cases, a torque applied to the proximal portion 106 can cause the anterior and posterior elements 204, 206 to pivot to the orient the bights 212, 220 on the ventricular side of the mitral valve zone C. As discussed above, the natural position of the catheter body 100 should align the procedure zone 120 substantially equally spaced from medial and lateral edges of the mitral valve opening. Thus the clinician can focus efforts on angular orientation of the anterior and posterior elements 204, 208, which orientation can be achieved with as few as one degree of freedom of movement.

Figure 7:
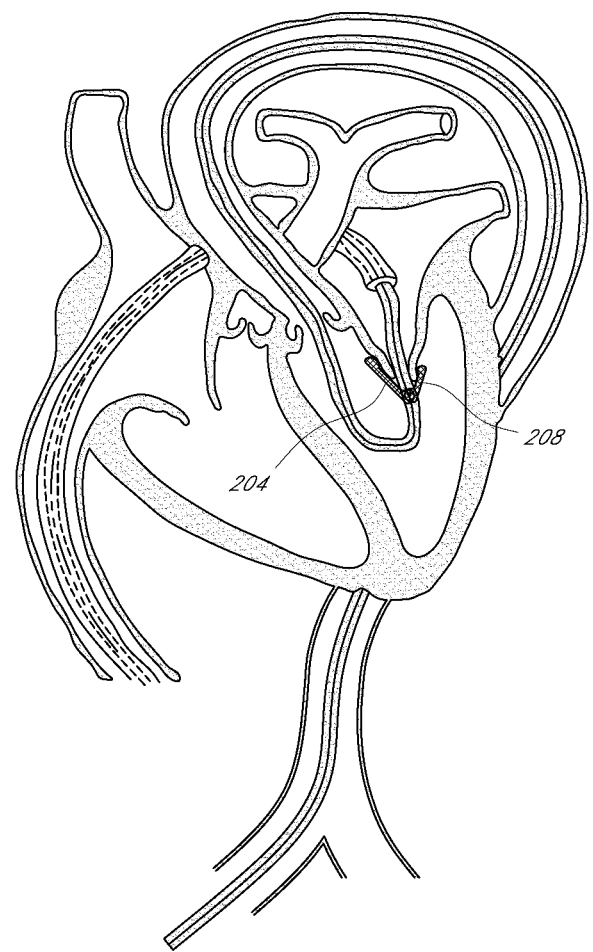
FIG. 7 is an image similar to that of FIG. 4, showing full engagement of a valve treatment device.

FIG. 7 illustrates a technique in which both leaflets 3, 4 are captured by the valve repair device 200. As discussed in connection with the incorporated matter, the device 200 captures the leaflets 3, 4 by actuating the elements 204, 208 toward the hub 216 to close the bights 212, 220. Various closure mechanisms can be used. For example, a spring hinge 218 can be disposed between the hub 216 and one or both of the anterior and posterior elements 204, 208. The spring can be store strain energy in the open state, e.g., when bights 212, 220 are enlarged and in a free state when the bights 212, 220 are closed. Alternatively, wire-actuated mechanisms can be disposed in the valve repair device 200 and/or the catheter 100 to pull the anterior and posterior elements 204, 208 against the hub 216 to close the bights 212, 220. As discussed below, the closure of the bights 212, 220 occurs sequentially, e.g., anterior bight 212 first and posterior bight 220 second. An advantageous design would involve closing the anterior bight 212 first because the anterior leaflet 3 is generally harder to catch. The range of motion of the anterior leaflet is greater and has a larger excursion, and thus is harder to catch. In some embodiments, as discussed in connection with FIGS. 10-14 below, the leaflets are captured between atrial and ventricular structures of the heart in a sandwich fashion.

Figure 8:
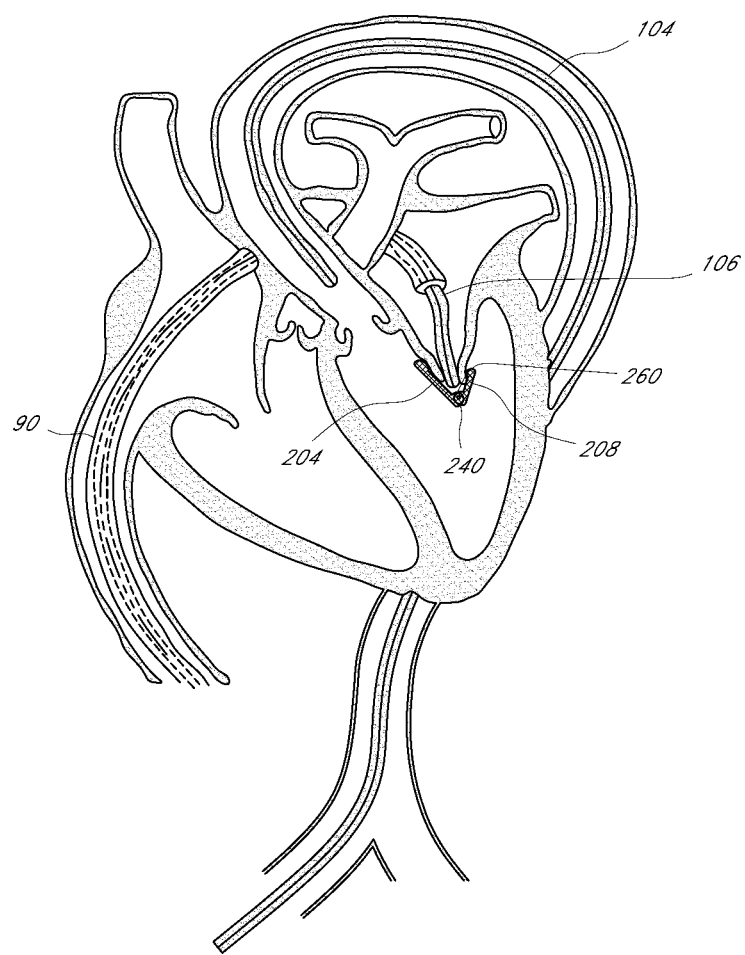
FIG. 8 is an image similar to that of FIG. 4, showing release of a distal portion of a delivery device from the valve treatment device, just prior to removal of the distal portion from the patient.

FIG. 8 shows that after the leaflets 3, 4 are captured, the valve repair device 200 can be de-coupled from the catheter 100 and left in place. The catheter 100 is then removed from the first and second access sites. In an initial decoupling step, the distal portion 104 of the catheter 100 can be decoupled from a distal interface 240 of the valve repair device 200 as described further below in connection with FIGS. 10 and 21.

Figure 9:
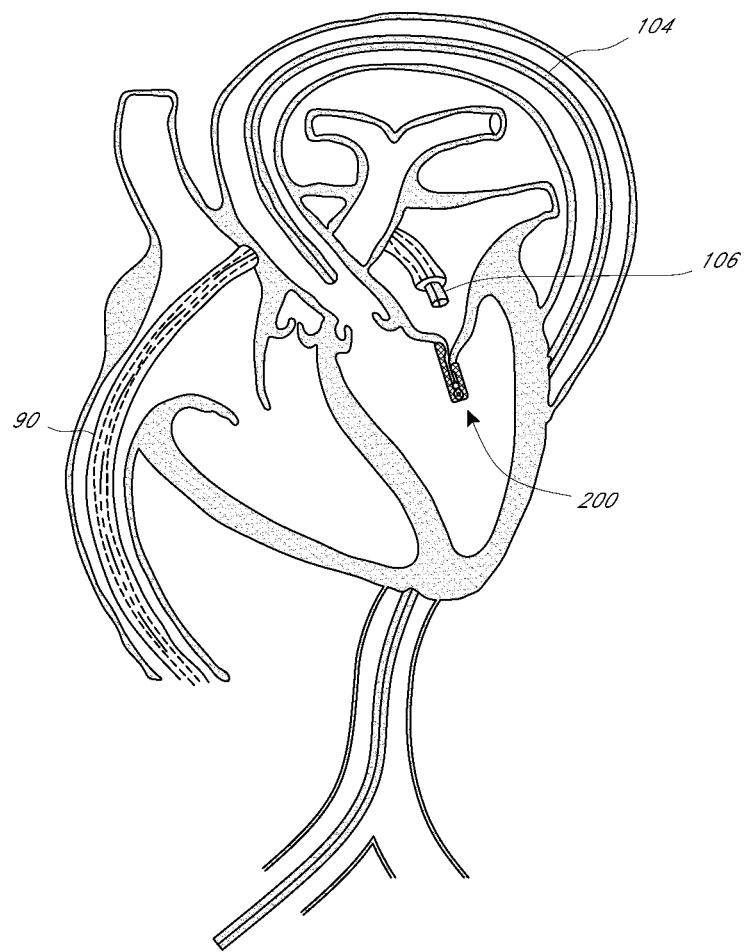
FIG. 9 is an image similar to that of FIG. 4, showing release of a proximal portion of a delivery device from the valve treatment device, just prior to removal of the proximal portion from the patient.

FIG. 9 shows that after the distal portion 104 is de-coupled from the valve repair apparatus 200 the proximal portion 106 can be de-coupled from the valve repair apparatus 200 as well. FIGS. 9 and 10 illustrate a proximal interface 260 that enables the valve repair apparatus 200 to be selectively separated from the proximal portion 106 of the catheter body. FIGS. 21-25C illustrate further examples among the variety of devices that can be used for the proximal interface 260.

II. Apparatuses Capturing and Holding Valve Leaflets

Further details of various implementations of the catheter 100 are discussed with reference to FIGS. 10 through 14. In one embodiment, the catheter 100 can include a device housing catheter 400 made of material flexible and torqueable, preferably of a polymeric material but any other biocompatible material may be used. The device housing catheter 400 contains a central lumen through which the valve repair deployment catheter 404 can be advanced, and has in its wall holes 408, 412 (herein referred to as "portals") that, once the housing catheter 400 is in place in the ascending aorta with the assistance of the orientation catheter, are specifically aligned with the locations of the anterior leaflet 3 and posterior leaflet 4 to allow for the deployment of the anterior and posterior elements 204, 208 incorporated into the deployment catheter 404 that unfold and project out of the apparatus to gather the individual leaflets, as discussed above. FIGS. 11-14 show that the mitral valve repair device 200 can include anterior and posterior atrial elements 204A, 208A for provide enhanced security of each leaflet. The housing catheter 400 can be configured to deploy the elements 204A, 204B through the same or different portals as the elements 204, 208. The deployment catheter 404 is a catheter with a central lumen for a guidewire G, is made of material flexible and torqueable, and has a semi-rigid portion that contains the valve repair device 200. As discussed above, the valve repair device 200 includes anterior and posterior elements 204, 208 and the spring hinge 218, and in some cases the atrial elements 204A, 204B. In an alternative embodiment, the housing catheter 400 and deployment catheter 404 may be incorporated into a single catheter with a movable core and may contain a central lumen for a guidewire.

Monitoring the advancement and manipulation of the device housing catheter 400 and the deployment catheter 404 may be done by a variety of visualization techniques including, but not limited to MRI, fluoroscopy, endoscopy, thoracoscopy, transthoracic, intracardiac, and transesophageal echocardiography. These and other visualization techniques are employed throughout the present invention to track the movement of the apparatus inside a human body.

FIG. 10-14 depict in longitudinal section one embodiment of the present invention for mitral heart valve repair showing the housing catheter 400, advanced through a sheath 90 placed as depicted in FIG. 3, over a guidewire and into the proper position between the mitral valve leaflets 3 and 4. The deployment catheter 404 with its incorporated valve repair device 200 has been advanced over a guidewire through the device housing catheter 400 and into proper position with respect to the mitral valve leaflets 3 and 4. Through advancement, retraction, and torqueing of the deployment catheter 404 by the operator, the deployment catheter allows the operator to manipulate the valve repair device. The function of the leaflet immobilization apparatus (including the anterior posterior elements 204, 208, spring hinge 218, and atrial elements 204A, 204B if present) is to clip or attach the anterior and posterior leaflets 3, 4 together. These components of the leaflet immobilization apparatus are preferably made of a sterile, biocompatible material such as a metal or plastic material known to be biocompatible. The leaflet immobilization apparatus is preferably cylindrical in shape, but may also be rectangular, conical or a multitude of other shapes. In mitral heart valve repair, the anterior element 204 may be longer than the posterior element 208, thus taking into account the anatomical difference in the size and shape of an anterior mitral valve leaflet 3 compared to a posterior mitral valve leaflet 4 as demonstrated in FIG. 2. By way of example, the shape of the anterior and posterior elements 204, 208 may resemble thin rectangular arms or wings that are connected by the hinge 218. However, the design of the anterior and posterior elements 204, 208 may be shaped in a variety of different forms. For example, the anterior and posterior elements 204, 208 may be circular, triangular, square, oval, or elliptical. The anterior and posterior elements 204, 208 may also be straight or curved. A cylindrical valve repair device with circular elements is discussed more in connection with FIGS. 16-20 below.

Differences in the sizes of the anterior and posterior elements 204, 208 may be tailored to the anatomical requirements of a particular surgical repair and patient. In any case, the shape of the anterior and posterior elements 204, 208 are designed to fit within the lumen of a catheter and, when deployed, to optimally interface with the unique anatomical shape of the anterior leaflet 3 and posterior leaflet 4, respectively. When the anterior and posterior elements 204, 208 are located outside the lumen of the catheter, the spring hinge 218 connecting the anterior and posterior elements 204, 208 extends the anterior and posterior elements 204, 208 outward and away from catheter system. The spring hinge 218 limits the range of movement of the anterior and posterior elements 204, 208 from a closed position, or zero degrees, to an open position not to exceed 90 degrees away from the catheter system. The spring hinge 218 exerts relatively little force against the anterior and posterior elements 204, 208 in the open position. When the anterior and posterior elements 204, 208 are contained within the lumen of the 400, the walls of the lumen force the anterior and posterior elements 204, 208 inward. In an alternative embodiment, the closed position of anterior and posterior elements 204, 208 may be maintained by a latch mechanism that can be released by an actuator in the proximal portion of the deployment catheter 404. Thus, in the lumen of the housing catheter, the anterior and posterior elements 204, 208 are flush within the housing catheter 400, and the spring hinge 218 is loaded with the force of the anterior and posterior elements 204, 208 in a closed position. To ease advancement of the deployment catheter 404 with its incorporated leaflet immobilization apparatus, the housing catheter 400 may contain grooves shaped to receive the anterior and posterior elements 204, 208, or to receive the deployment catheter 400 in a proper orientation so that the anterior and posterior elements 204, 208 are directed properly toward the portals 408, 412 in the housing catheter 400. In an alternative embodiment, the housing catheter 400 and the deployment catheter 404 with its incorporated leaflet immobilization apparatus may he incorporated into a single catheter with a moveable core that allows for the manipulation of the anterior and posterior elements 204, 208, the spring hinge 218, and atrial element 204A, 208A by actuator or actuators at the proximal end of the catheter system, or by direct manipulation of the core itself at the proximal end of the catheter system.

FIG. 10 thus depicts the deployment catheter 404 advanced within the housing catheter 400 and the anterior and posterior elements 204, 208 in closed positions. The deployment catheter 404 has been advanced within the housing catheter 400 so that the anterior and posterior elements 204, 208 are positioned below the ventricular aspect of the open anterior 3 and posterior 4 leaflets. The anterior and posterior elements 204, 208 are now ready for deployment.

FIGS. 10-13 sequentially depict one embodiment of independent deployment of anterior element 204. In FIG. 10 the deployment catheter 404 is shown advanced toward the distal end of the housing catheter 400 that has an anterior portal 208. The proximal end of deployment catheter 404 may extend outside the proximal end of the housing catheter 400. This enables the operator to push and pull the deployment catheter 404 in a distal or proximal direction within the catheter. As the operator pulls the catheter 404 in the proximal direction, the valve repair device (including of the anterior and posterior elements 204, 208, and the spring hinge 218) moves in a proximal direction within the housing catheter 400. In addition, gradually, the anterior element 204 independently extends outward from the anterior portal 408 as the entire length of the anterior element 204 moves proximally toward the open space of the anterior portal 408 of the housing catheter's 400. The anterior element 204 independently extends outward first because of the differential lengths of anterior element 204 and posterior element 208 and because of the differential locations of the anterior portal 408 and the posterior portal 412. Without the containment of the lumen walls of the housing catheter 400, the force of the loaded spring hinge 218 extends the anterior element 404 through the anterior portal 408 of the housing catheter 400 away from the deployment catheter 404.

Figure 12:
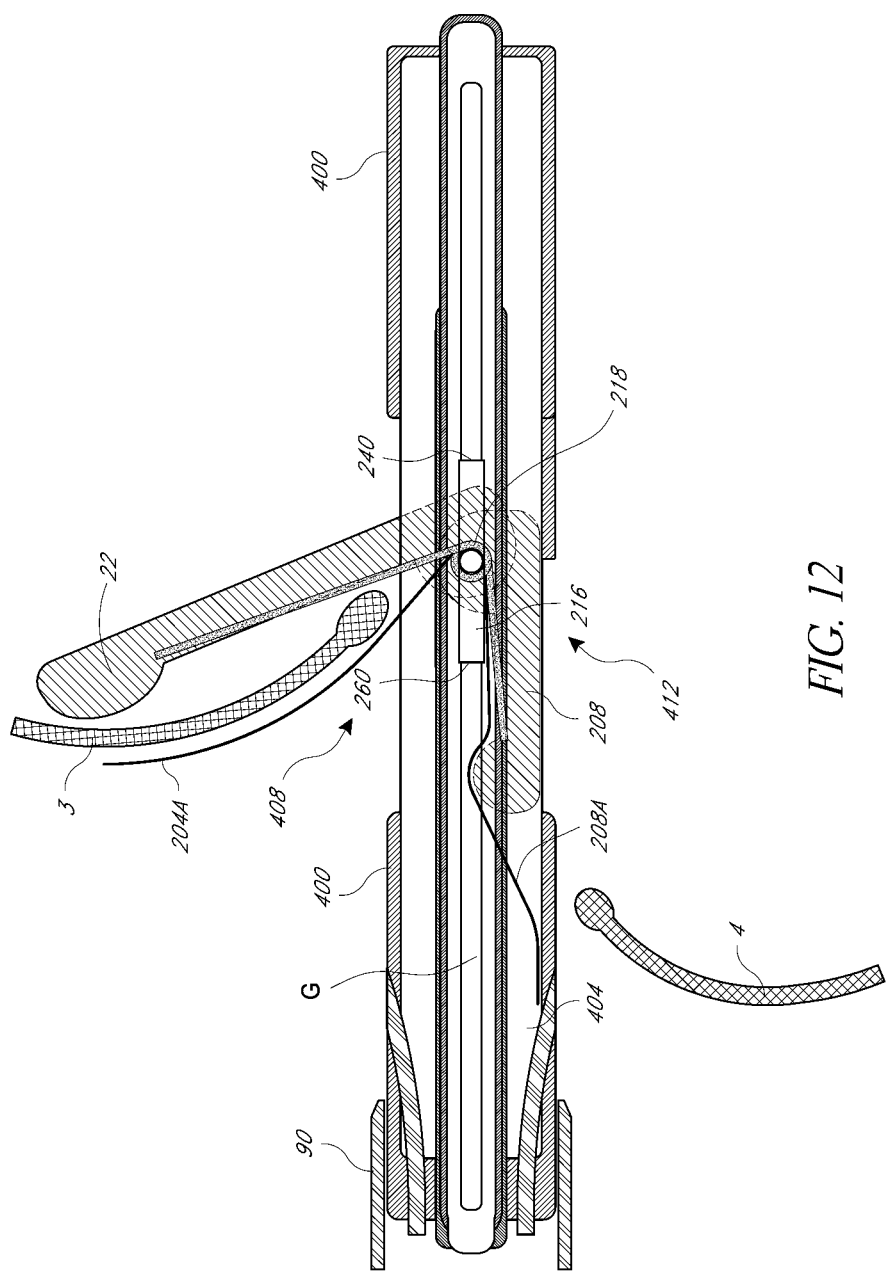

In an alternative embodiment, an operator may release the anterior element 204 or actuate the deployment of the anterior element 204 by way of an actuator located at the proximal end of the deployment catheter 400. Referring back to FIG. 1, the tips of the mitral valve leaflets 3 and 4 point in a ventricular direction when open. Thus, the angle of the deployed anterior element 204 allows for the engagement of the ventricularly directed anterior valve leaflet 3. Incorporating the frame of reference of FIG. 1 regarding the mitral valve leaflets 3 and 4, FIG. 11 shows the anterior element 204 free from the lumen of the housing catheter 400 and in a partially extended position below the anterior mitral valve leaflet 3. FIG. 12 next shows the anterior element 204 in a fully extended position below the anterior leaflet 3, and engaging the anterior leaflet 3. Once the anterior element 204 is fully extended and positioned below the anterior leaflet 3, the flexible and torqueable nature of the housing catheter 400 and the deployment catheter 404 allow the operator to move and adjust the housing catheter/deployment catheter system until the anterior element 204 is determined to be positioned optimally below the anterior leaflet 3, using imaging techniques such as fluoroscopy, MRI, transesophageal, intracardiac, transthoracic, or three-dimensional echocardiography as needed.

The atrial element 204A, if present, can be deployed as illustrated in FIGS. 11 and 12. In particular in FIG. 11, the element 204A is retained within the housing catheter 400. Relative proximal movement of the housing catheter 400 moves the element 204A into the portal 408. When disposed in the portal the element 204A can swing open to the position shown in FIG. 12. Although spaces are shown between the element 204A and the anterior leaflet 3 and between the leaflet 3 and the anterior element 204, in various embodiments these structures are closely sandwiched together. In particular, the element 204A can be configured to be biased to swing oven to a larger extent than the element 204. However, due to the rigidity of the element 204, the element 204A will press up against and conform to the surface of the element 204. This will result in a force being applied to the leaflets. Although shown as smooth surfaces, one or both of the elements 204, 204A can have barbs or other structures suitable for enhancing engagement with the valve tissue. Some of such structures are set forth in the incorporated subject matter of the Appendix.

Figure 14:
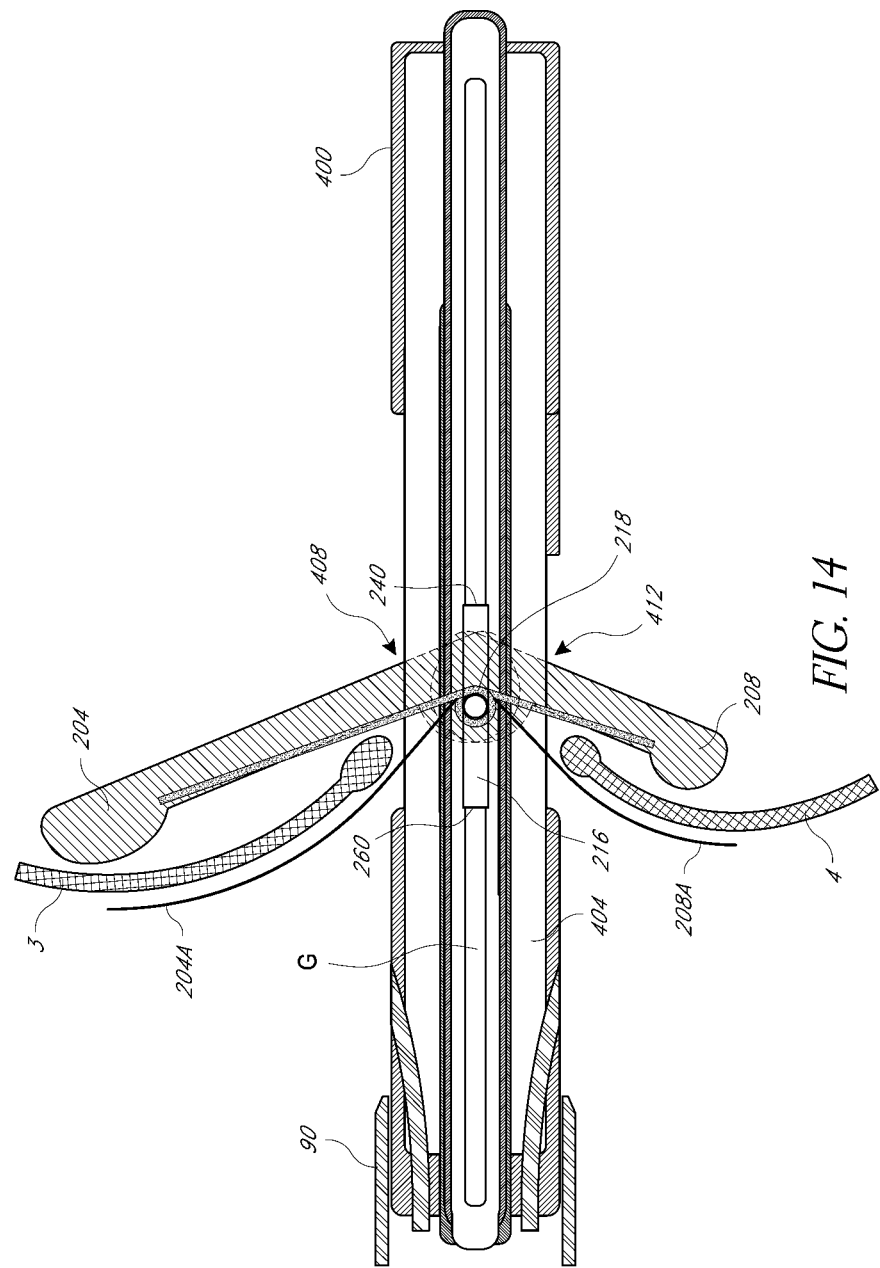
Figure 15:
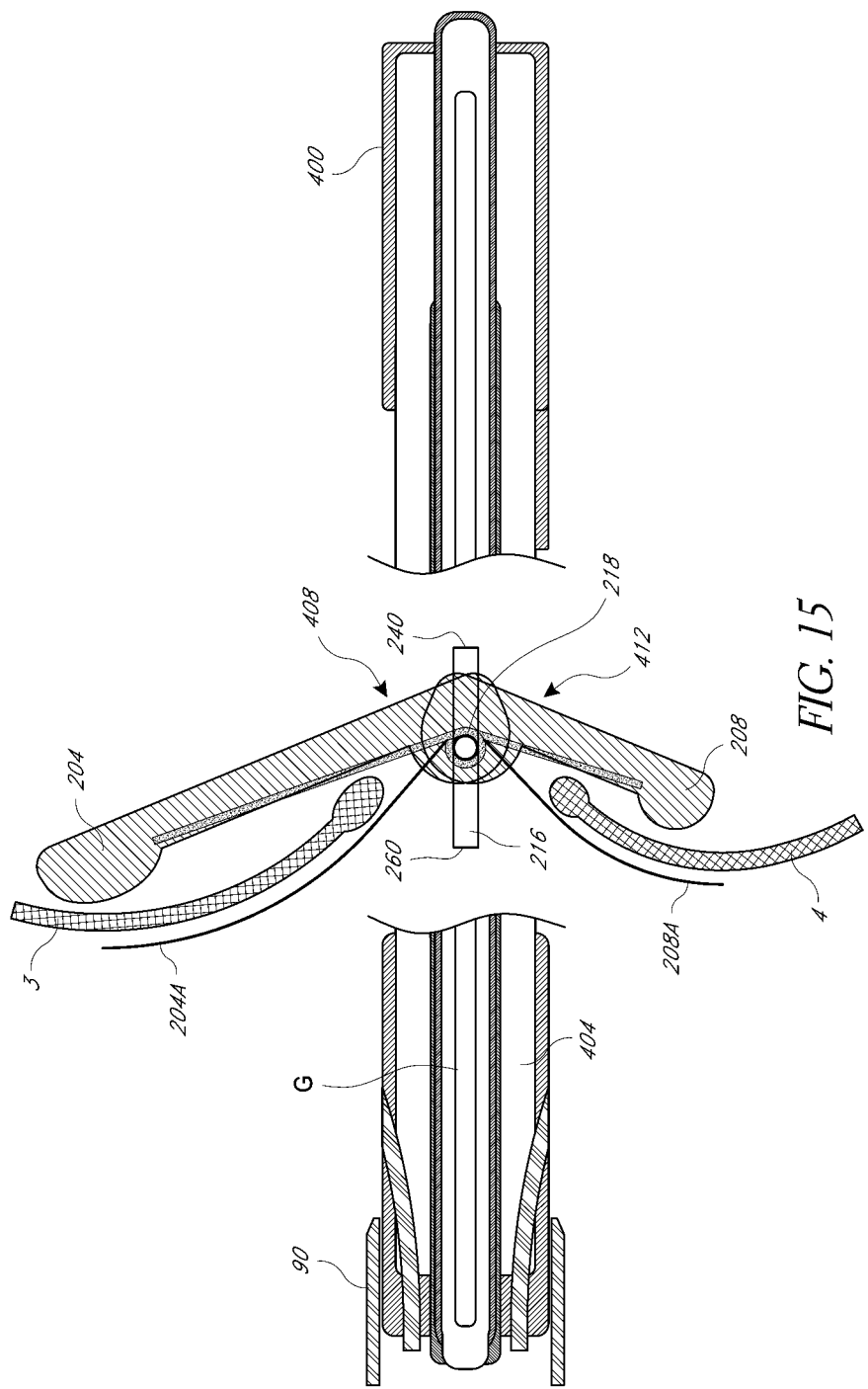

FIGS. 13 and 14 sequentially depict one embodiment of the present invention showing the independent deployment of posterior element 208. Once the anterior element 204 extends through the anterior portal 408, the operator may further pull the deployment catheter 404 in a proximal direction. This movement will cause the posterior element 208 to move in the lumen of the housing catheter 400 to the opening of the posterior portal 412. In one technique, the atrial element 208A may thereafter be deployed to sandwich the leaflet 4 between the elements 208, 208A. The posterior element 208 may be shorter than the anterior element 204 taking into account the size difference of the anterior leaflet 3 and posterior leaflet 4 of the mitral valve. Similar to the independent deployment of anterior element 204, the posterior element 208 gradually and independently springs to an open position as the operator pulls the deployment catheter 404 proximally. In an alternative embodiment of the present invention, an operator may actuate the release and/or deployment of the posterior element 208 by way of an actuator located at the proximal end of the deployment catheter 404. In FIG. 13, the posterior element 208 is shown in a partially extended position shortly after clearing the lumen of the housing catheter 400 through the posterior portal 412. Similar to anterior element 204 positioning, the posterior element 208 is positioned at the ventricular side of posterior leaflet 4. In FIG. 14, the posterior element 208 is in a fully deployed position and is optimally positioned under posterior leaflet 4.

The atrial element 208A, if present, can be deployed as illustrated in FIGS. 13 and 14. In particular in FIG. 13, the element 208A is retained within the housing catheter 400. Relative proximal movement of the housing catheter 400 moves the element 208A into the portal 412. When disposed in the portal the element 208A can swing open to the position shown in FIG. 14. Although spaces are shown between the element 208A and the posterior leaflet 4 and between the leaflet 4 and the anterior element 208, in various embodiments these structures are closely sandwiched together. In particular, the element 208A can be configured to be biased to swing oven to a larger extent than the element 208. However, due to the rigidity of the element 208, the element 208A will press up against and conform to the surface of the element 208. This will result in a force being applied to the leaflets. Although shown as smooth surfaces, one or both of the elements 208, 208A can have barbs or other structures suitable for enhancing engagement with the valve tissue. Some of such structures are set forth in the incorporated subject matter of the Appendix.

III. Structures for Distal Release of a Valve Repair Device

The distal and proximal interfaces 240, 260 are shown in only some of the figures for the sake of keeping the other drawings simpler. These structures and the hub 216 of which they are a part, or an analogous variation, can be present in the embodiments illustrated in the other figures as well. Preferably the distal interface 240 is one that is secure but configured to detach the distal portion 104 of the catheter 100 from the repair apparatus 200. In one embodiment, the distal portion 104 includes an outer catheter body that extends between the distal end of the distal portion and a proximal end of the distal portion. Inside the catheter body, a lumen carries an inner sleeve that bridges between the distal interface 240 and the proximal end of the catheter body. The inner sleeve can comprise and an elongate body that has in outer surface that slideably engages the inner lumen of the catheter body. If the distal portion 104 is to be delivered over a guidewire, the inner sleeve can include an elongate lumen extending therethrough from the distal end of the distal portion 104 to the proximal end of the distal portion.

To detach the distal portion 104 from the distal interface 240 of the valve repair apparatus 200 one can provide distal relative movement of the inner sleeve relative to the catheter body of the distal portion 104. This removes the unifying force of the inner sleeve and permits the distal interface 240 to separate from the proximal end of the distal portion 104. For example, a lateral movement of the proximal end of the distal portion 104 relative to the distal interface 240 can separate these structures from each other permitting the distal portion to be withdrawn. In another embodiment, the inner sleeve can be provided on the outside of the proximal end of the distal portion 104 and can extend proximally of the distal interface 240.

Many variations of mechanisms to deploy devices are discussed in U.S. Pat. No. 8,216,256, which is hereby incorporated by reference herein in its entirety.

The proximal interface 260 can be configured similar to the distal interface 240 or as discussed in the '256 patent or can have another configuration. In one variation, the proximal interface 260 operates by providing a torque to a proximal structure carried by the proximal portion 106 of the catheter 100. In particular, the proximal portion 106 can include a catheter body with a lumen extending therethrough. A cylindrical sleeve can be disposed within the lumen of the catheter body. The sleeve can be configured to securely retain the valve repair apparatus 200 at the proximal interface 260. For example, the proximal interface 260 can include a tubular body disposed on the central hub 216 having internal threads disposed thereon. The distal end of the inner sleeve can be threaded to match the internal threads of the proximal interface 260. Accordingly, relative rotation of the inner sleeve relative to the catheter body of the proximal portion 106 can result in separation of the valve repair apparatus 200 from the proximal portion 106. Further details of threaded connections for detaching deployable devices within a body lumen or cavity are discussed in U.S. Pat. No. 7,226,467, which is incorporated by reference herein.

Among the many variations, the structures for disconnecting the valve repair apparatus 200 from the proximal and distal aspects of the catheter 100 can be of the same type. The structures described as being used for the proximal interface 260 can be used for the distal interface 240, and those described for the distal interface can be used for the proximal interface.

The procedure may be or may include a diagnostic procedure. It may comprise an imaging procedure, or a hemodynamic monitoring procedure. For example, an imaging device 500 can be disposed in the catheter 100. The imaging device 500 includes an ultrasound transducer 504 and a movement device 508 coupled with the transducer 504. The movement device 508 enables the transducer 504 to move relative to the procedures zone 120 such that a segment of the anatomy along the procedure zone can be imaged. In one example, the movement device 508 comprises a rotatable member that is disposed in the lumen 130. The rotation enables the transducer 504 to obtain imaging data about the catheter 100. FIG. 10 shows the movement device 508 positioned inside the guidewire G. In variations, the guidewire and the movement device 508 can be positioned sequentially, for example removing the guidewire G prior to the insertion of the movement device 508. In other embodiments, separate lumens are provided for the guidewire G and the movement device 508 within the catheter 100. Preferably the movement device 508 is also able to translate to move the transducer axially to provide imaging along a length. An example of an imaging device is discussed in U.S. 2006/0259137 A1, published November 2006, which is incorporated by reference herein.

The movement device 508 can be configured to be operated from either one or both of the first and second access sites discussed above. For example, one or both of the distal end and the proximal end of the translation device 508 can be configured to be coupled with an actuator to provide rotation and/or translational movement of the transducer 504. In various methods the transducer is advanced from the arterial access site to a location upstream of the valve being treated. An anatomical segment including, for example, the mitral valve is imaged from upstream to downstream. Thereafter an appropriate step is taken, such as a medial-lateral adjustment of the position of the valve repair device 200 along the valve. For example, with respect to FIG. 4A, the catheter can be torqued to move the device 200 closer to the center of the box C. The imaging device 500 is then withdrawn toward the arterial access site so that the repair device 200 can be detached from the distal portion 104. Thereafter, the distal portion 104 and the imaging device 500 can be removed from the arterial access site, either together or sequentially.

A similar approach could be directed from the venous access site. In this approach, the imaging device 500 can be advanced through the catheter 100 to the just proximal of the valve. Then, the imaging device 500 can be activated to gather imaging data, for example while rotating and traversing a valve and an adjoining anatomical region of interest. Thereafter the imaging device 500 is withdrawn to a location proximal of the repair device 200 so that the repair device can be separated from the proximal portion 106 of the catheter 100. Subsequently, the proximal portion 106 and the imaging device 500 are withdrawn together or sequentially.

IV. Enhanced Valve Prostheses

FIGS. 16-19 and 21-25C illustrate further embodiments of implants having improved coupling with valve leaflets. In particular, FIGS. 16-19 show a valve repair prosthesis 600 with curved leaflet grasping elements. The prosthesis 600 is configured to be deployed from a catheter assembly or system, such as the catheter 100 or the catheter system 800 shown in FIG. 20. As discussed above, the catheter 100 can be delivered over a guidewire. Similarly, the prosthesis 600 can have a lumen (not shown) extending entirely therethrough for passage of a guidewire. Or, a side lumen may be provided on the catheter 100 such that no dedicated guidewire lumen is provided on the prosthesis.

The prosthesis 600 comprises a prosthesis body 604 that extends between proximal and distal ends 608, 612. Some or all of the prosthesis body 604 can be metallic, e.g., a biocompatible metal. Suitable metals include any one of or any combination of nickel, titanium, stainless steel and other biocompatible radiopaque metals and materials. The prosthesis 600 comprises a base 616 in a central position and a plurality of grasping element 620, 624 disposed laterally of the base 616. The grasping elements 620, 624 can be identical, but in certain embodiments have different configurations such as by making the grasping element 620 shorter such that it is adapted to capture a typical posterior leaflet and making the grasping element 624 longer such that it is adapted to capture a typical anterior leaflet. The posterior element 620 may be configured in a variety of ways to better grasp the anterior leaflet 3. In various patient conditions, the posterior leaflet varies from a typical un-diseased condition such that a longer or shorter leaflet grasping element may be advantageous. The posterior element 620 can have a length of between about 5 and about 15 millimeters in some embodiments. The posterior element 620 can have a length of between about 7 and about 13 millimeters in some embodiments. The posterior element 620 can have a length of between about 8 about 12 millimeters in some embodiments. The posterior element 620 can have a width between about 2 and about 7 millimeters in some embodiments. The posterior element 620 can have a width of between about 3 and about 6 millimeters in some embodiments. The posterior element 620 can have a width of between about 4 about 6 millimeters in some embodiments. The anterior element 624 may be configured in a variety of ways to better grasp the posterior leaflet 4. In various patient conditions, the anterior leaflet varies from a typical un-diseased condition such that a longer or shorter leaflet grasping element may be advantageous. The anterior element 624 can have a length of between about 5 and about 15 millimeters in some embodiments. The anterior element 624 can have a length of between about 7 and about 13 millimeters in some embodiments. The anterior element 624 can have a length of between about 8 about 12 millimeters in some embodiments. The anterior element 624 can have a width between about 2 and about 7 millimeters in some embodiments. The anterior element 624 can have a width of between about 3 and about 6 millimeters in some embodiments. The anterior element 624 can have a width of between about 4 about 6 millimeters in some embodiments. Each of the grasping elements 620, 624 can include an elongate member articulated to the body 604 and thus may be considered to be arms of the prosthesis 600.

The prosthesis 600 is elongate in certain embodiments, e.g., having a larger longitudinal dimension between the proximal and distal ends 608, 612 than a dimension transverse to the longitudinal dimension. The prosthesis 600 has a generally cylindrical configuration with a circular profile in transverse cross-section (taken perpendicular to a longitudinal axis). The cylindrical profile enables the prosthesis 600 to rotate in a catheter system or in a sheath, such as any of the catheter systems discussed herein, to orient the prosthesis circumferentially in the catheter system or sheath. This allows the rotational position of the prosthesis 600 to be changed within a circular lumen of a delivery catheter or sheath, e.g., to rotate the grasping element 620, 624 toward or away from windows or portals in the catheter body 100.

The posterior and anterior elements 620, 624 are coupled with the central base 616. In certain embodiments, the posterior element 620 can be coupled with the base 616 at a distal portion thereof. A hinge connection 632 can be provided between a distal portion 636 of the posterior element 620 and a distal portion 638 of the base 616. Similarly, the anterior element 624 can be coupled with the base 616 at a distal portion 640 thereof. A hinge connection 644 can be provided between a distal portion 648 of the anterior element 624 and the distal portion 652 of the base 616.

The hinge connections 632, 644 advantageously are disposed away from each other to help maintain the small size of the prosthesis. In certain embodiment, the hinge connection 632 to the posterior element 620 is disposed at a single location adjacent to the distal end 612 at a first position of the circumference of the prosthesis 600. In certain embodiment, the hinge connection 644 to the anterior element 624 is disposed at a second position adjacent to the distal end 612 of the prosthesis 600. The first and second positions preferably are offset by at least 45 degrees and in some cases 90 degrees or more. The hinge connection 644 can include a plurality of pivot points, e.g., one on each side of the prosthesis 600.

In one embodiment, the anterior element 624 is disposed on a first side of the prosthesis and the posterior element 620 is disposed on a second side of the prosthesis opposite the first side. By positioning the elements on opposing sides, the elements 620, 624 are configured to have their point of largest movement in a plane transverse to the line of coaptation of a valve when applied. The anterior element 624 can have a hinge connection 644 that includes two pivot points on opposite sides of the prosthesis 600. The hinge connection 632 to the posterior element 620 can be at a single location spaced apart from one or both connection points of the hinge connection 644.

Figure 16:
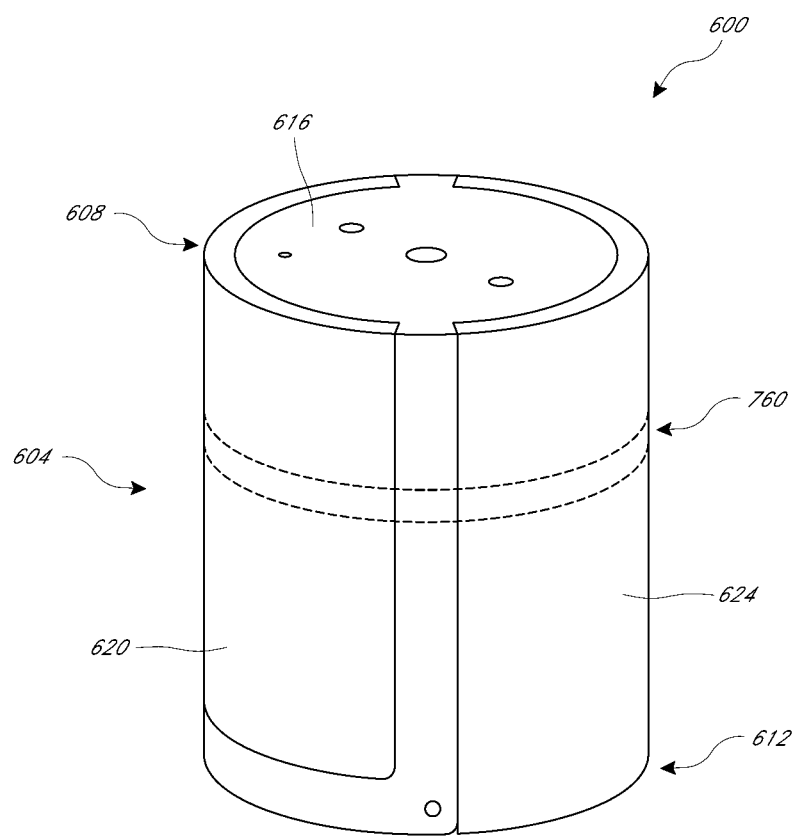
FIGS. 16-19 illustrate aspects of valve prostheses that enhance coaptation compared to conventional prostheses.
Figure 17:
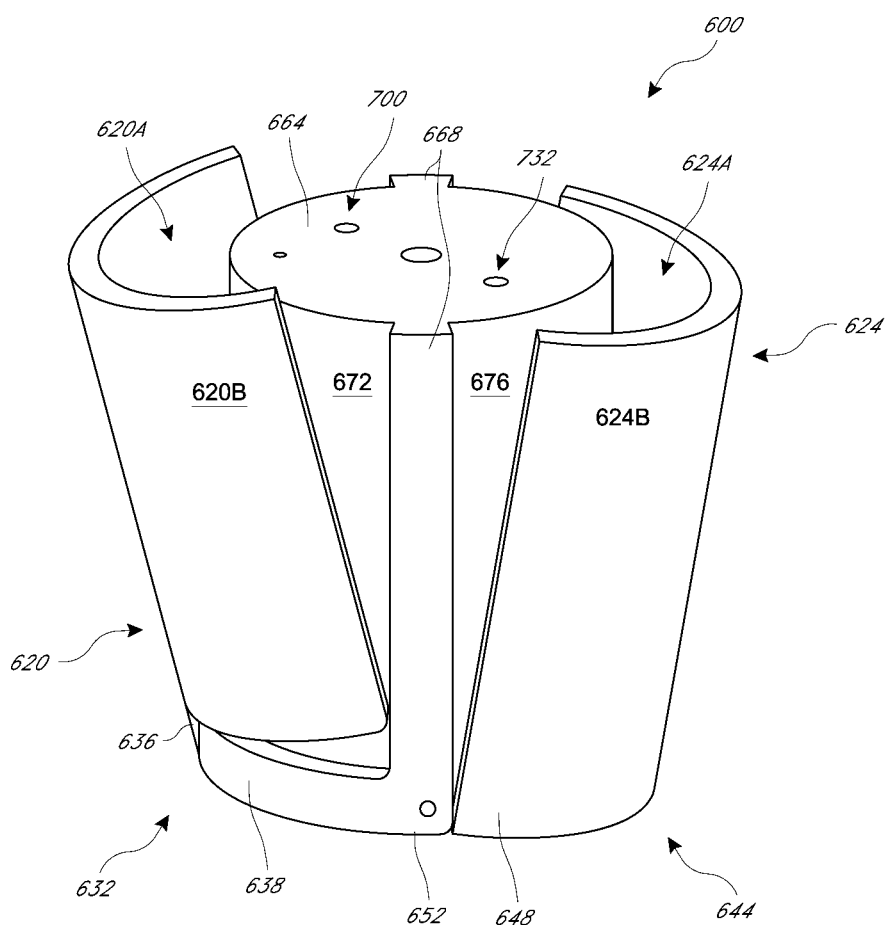

The prosthesis 600 is configured such that the hinge connections 632 644 move the grasping elements 620, 624 from a closed position (FIG. 16) to an open position (FIG. 17). In the open position the elements extend away from the base 616 at least at a proximal ends thereof. In the closed position the element 620, 624 are in a flush position relative to the base 616. The base 616 can be configured to facilitate the flush arrangement. For example, the base 616 can include a substantially cylindrical core 664 with lateral protrusions 668 extending from a periphery of the core 664. The protrusions 668 can extend longitudinally along at least a portion of, e.g., along the entire core 664. In one embodiment, the protrusions 668 comprise a flange on one or both sides of the core 664. The core 664 can have a first outer surface 672 matching an inner side 620A of the posterior element 620 and a second outer surface 676 matching an inner side 624A of the anterior element 624. The matching surfaces enable the elements 620, 624 to rest very close to the base 616 providing little or no gap therebetween in the closed position. A proximally facing shoulder extending from the lateral protrusions circumferentially toward the hinge connection 632 has a radial with that is about the same as the thickness of the anterior element 624 such that the element 624 is received in a flush arrangement relative to the shoulder.

One or both of the surfaces 620A, 624A are textured, coated, or otherwise processed to maximize frictional engagement with the leaflet tissue. One or both of the surfaces 672, 676 are textured, coated, or otherwise processed to maximize frictional or other engagement with the leaflet tissue. The surfaces on the outer sides 620B, 624B preferably are flush with the radially outer surface of the protrusions 668 of the core 664 in the closed position. This arrangement facilitates reducing or minimizing the size of the delivery catheter by reducing or minimizing gaps between the outer surfaces 620B, 624B and the inner wall of the catheter body in which the prosthesis 600 resides.

Figure 18:
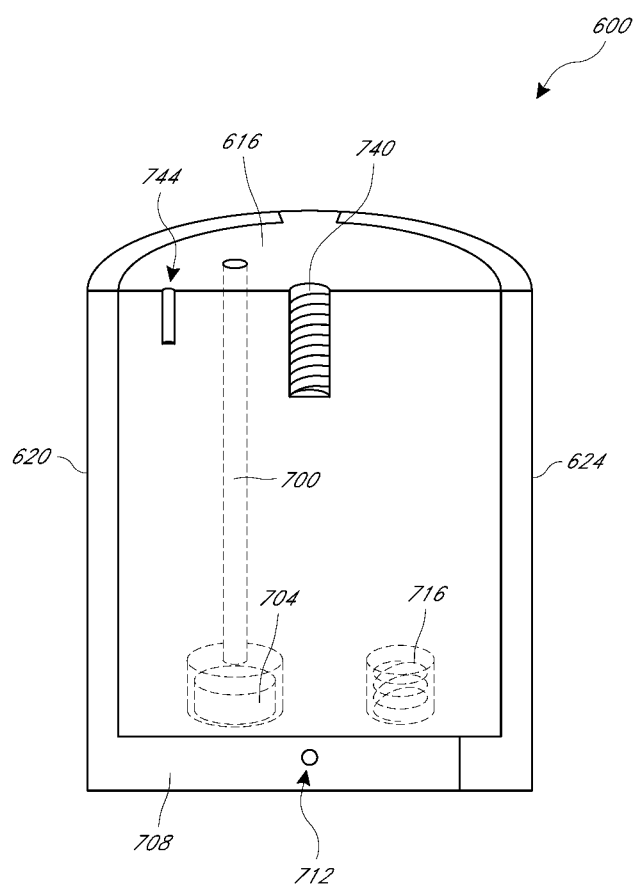

The prosthesis 600 is configured such that the posterior and anterior elements 620, 624 can be actuated independently. Such actuation can be by any suitable mechanism or technique. In one embodiment, the posterior and anterior elements 620, 624 are actuated pneumatically. FIG. 18 shows that a control channel 700 can be provided in the base 616, e.g., in the core 664 to provide for remote control, e.g., actuation of the gripping elements 620, 624. For example, the control channel 700 can provide fluid communication between a source of control fluid and a distal end of the control channel 700, e.g., in a pneumatic or hydraulic configuration. This enables a driving fluid, which can include one or more of saline, water, heparin, radiopaque contrast, or other biocompatible liquid, to flow into the prosthesis 600. In certain embodiments, the control channel 700 is configured to convey within the prosthesis 600 a gas such as one or more of nitrogen, air, carbon dioxide, oxygen, or other gases that area highly soluble in blood or otherwise biocompatible. The control channel 700 could be coupled with a source of any of these control fluids or with other inert synthetic fluids, particularly those that have low toxicity and high solubility for gas, e.g., any suitable perfluorocarbon. In one embodiment, the channel 700 is in fluid communication with an actuator 704 disposed at the distal end of the channel 700. The actuator 704 can be or can comprise a portion of a piston. A distal face of the actuator 704 is engaged with or is in position to drive a portion of the posterior element 620. In one embodiment, the distal portion of the posterior element 620 comprises a flange 708 that extends from the outer periphery of the prosthesis across the distal end of the prostheses 612 to a pivot 712. The actuator 704 is configured to act on the flange 708 at a location between the pivot 712 and the outer periphery of the prosthesis 600.

The control channel 700 could be configured to have mechanical control elements disposed therein. For example, the actuator 704 can be engaged with a wire or other compression or tension member that is able to push on the actuator. As the compression or tension member is moved in the control channel 700 the actuator 704 acts on the flange 708 in certain embodiments. FIGS. 21-25c illustrate further fluid actuated configurations. In certain embodiment, a compression or tension member (e.g., a wire) is directly engaged with the flange 708 or another part of the gripping element 620 to directly actuate the element 620. The compression or tension member (e.g., a wire) preferably is able to be disengaged from the prosthesis 600 upon release of the prosthesis from the catheter assembly in which it is delivered.

Figure 19:
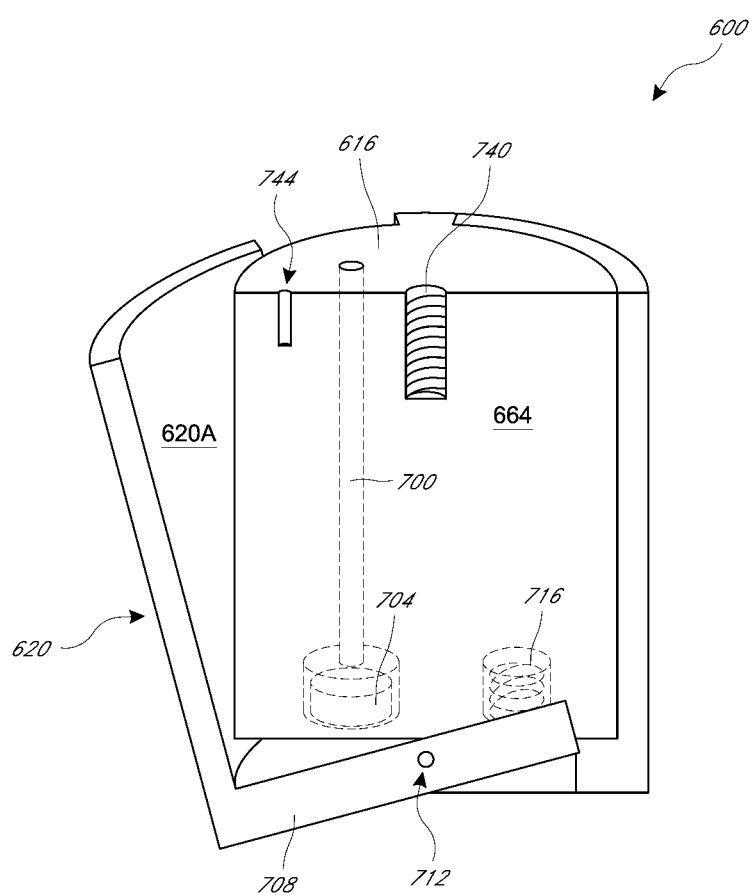

The posterior element 620 can be configured to be biased toward the closed position of FIGS. 16 and 19. In one example, a spring 716 is provided between the posterior element 620 and a portion of the prostheses to push the posterior element 620 toward the close position, e.g., to push the surface 620A toward and into engagement with the outer surface 672. FIGS. 23a-23c illustrate other ways to bias the posterior and/or anterior elements 620, 624 toward a closed position.

Although the details of the structures for actuating the anterior element 624 is not shown in cross-section, the anterior element can be actuated in a manner similar to the posterior element 620. In particular, a channel 732 can be provided that opens to the proximal end 604 of the prostheses. The channel 732 can communicate with another actuator similar or the same as the actuator 704 to move the surface 624B away from the surface 676. The anterior element 624 can be biased toward the closed positions of FIGS. 16 and 18 by a spring or other biasing member.

The prosthesis may also have features for connecting the prosthesis 600 to a catheter or catheter system 800 (see FIG. 20) or the catheter 100 described herein. For example, the prosthesis 600 may have a threaded recess 740 extending from the proximal face of the base 616. The threaded recess 740 enables connection to a catheter device or system, such as a pusher disposed in a catheter body. The pusher can help in positioning the prosthesis at the mitral valve for example. FIGS. 21-25c illustrate further structures that facilitate detachable connection between a proximal portion of a prosthesis and a delivery system. The prosthesis 600 also can have an indexing feature 744 configured to align the prosthesis 600 in a specific orientation relative to a catheter body in which the prosthesis is delivered. In one form, the indexing feature 744 comprises a recess configured to receive a pin or other protrusion of a delivery catheter. The indexing feature 744 can be a blind hole. In some embodiments the indexing feature 744 includes threads or other engagement features. In some embodiments the indexing feature 744 is able to both index the orientation of the prosthesis 600 relative to a catheter body and to releasably secure the prosthesis during delivery. FIGS. 21-25C illustrate further features for orienting a prostheses for deployment.

In certain embodiments, the prosthesis 600 is configured to be indexed to a catheter body without a dedicated indexing recess. Reducing the number of recesses or eliminating them completely can improve the biocompatibility of the prosthesis 600. For example, reducing or eliminating such features can reduce the chance of embolism because recesses may be a site for blood clot formation. Thus the indexing feature can include structures such as matched surface contours, temporary or low to moderate strength adhesives, frictional engagement, paired permanent magnets, and other engagement features. Matched surface contours can include a convex surface (e.g., on the proximal end 608 of the prosthesis body 604) and a concave surface (e.g., on the distal portion of a catheter body component disposed to engage the proximal end 608). The concave and convex surfaces can be configured with local apices offset from the geometric center of the proximal surface of the core 664.

Another use of these indexing features is to provide a counter-force in disengaging the prosthesis 600 from a catheter system in which it is delivered. In certain embodiments, the threaded recess 740 is unscrewed from a threaded member disposed in a catheter assembly used for delivering the prosthesis 600. The indexing feature 744 can provide a counter-force in certain embodiments. That is, an indexing structure of a catheter assembly engaged with the indexing feature 744 applied a torque opposing the torque generated by backing the threads of the catheter assembly threaded member out of the threads of the threaded recess 740.

Although not shown, the distal end 612 of the prosthesis 600 can also include and indexing feature and/or a threaded recess. A distal threaded recess can enable detachment of a threaded member extending in the distal portion 104 of the catheter 100 in the manner discussed above or from the catheter system 800. FIGS. 21-25C illustrate further structures that facilitate detachable connection between a distal portion of a prosthesis and a delivery system. A distal indexing feature can be used for counter torque when a threaded member is detached from a distal threaded recess. In some techniques the indexing feature 744 can be used for counter torque when a threaded member is detached from a distal threaded recess. In other variations, the indexing feature 744 is omitted and an indexing feature is disposed only on the distal end 612 of the body 604.

FIG. 16 shows that the prosthesis 600 can include as a further optional feature a retention member 760 configured to be disposed about the body 604. The retention member 760 may be a circumferentially applied band of material to retain the prosthesis 600 in the closed position. The retention member 760 may be made of solid bulk material, a woven material, or a constructed material such as a stent. The retention member 760 may be placed over and pushed along the length of the distal guidance rail with a retention member-applying catheter until the retention member 760 is applied to the prosthesis 600 at the mitral valve level. The retention member 760 is shown in dashed lines for clarity. In some embodiments, the retention member is provided to enhance the security of the grasping elements 620, 624 when the prosthesis is applied. The retention member 760 can be an elongate elastic member that can be stretched to be moved over the outside of the body 604. The elasticity of the member 760 is preferably sufficient to apply a circumferential compressive force onto the outer surface of the grasping elements 620, 624. The compressive three is sufficient to increase the forces applied by the grasping elements 620, 624 to a layer of valve tissue disposed between the faces 620A and 672 and/or the faces 624A and 676.

The retention member 760 can be disposed on either the proximal or distal portion of the catheter 100. For example, in one embodiment, the retention member 760 is dispose don the distal portion 104 and can be urged over the distal end 612 of the body 604 after the leaflets 3, 4 have been grasped. Transferring the retention member 760 from an outside surface of the distal portion 104 onto the outside surface of the body 604 can be accomplished in any manner. For example, the distal portion 104 can include a sheath disposed over an inner body. The sheath can have an end closes to the prosthesis 600. The end can abut an end of the retention member 760. The abutting relationship will provide that as relative motion is provided between the sheath and the inner body (e.g., the sheath urged toward the mitral valve leaflets, the retention member 760 will also be urged off of the inner body and onto the body 604 of the prosthesis 600. In another embodiment, the retention member 760 can be disposed in or on the portion 106. The retention member 760 can be disposed on an outside surface of the proximal portion 106 and can be urged distally by a sheath disposed around the outside surface. The retention member 760 can be used with the prostheses 858, discussed below.

The prosthesis 600 can be positioned at a heart valve, e.g., within the mitral valve, using a wire or catheter guidance rail that is fixed at both ends in a position external to the body, as discussed above. The placement can be facilitated by providing both venous and arterial placement. In one technique, initial placement is provided similar to FIG. 3. For example, access is provided to a peripheral venous site. Any standard technique can be used to cross the atrial septum. For example, a guide catheter or sheath 90 can be provided. Alternatively, a proximal portion can have a obturator or dilator for passing the proximal segment through the atrial septum.

The venous segment is then advanced across the mitral valve into the left atrium, through the left ventricle, across the aortic valve, and through the ascending and descending aorta away from the heart. The venous segment, which may be similar to the proximal portion 106, may include one or more internal lumens to facilitate injection of pharmaceutical or contrast agents or passage of a guidance wire, and may include structural features intended to allow the tip to be directed by blood flow such as a balloon, as discussed above.

An arterial segment can be provided by a suitable technique. For example, FIG. 3A shows an arterial segment 104A can be placed percutaneously through an arterial access site and advanced toward the distal tip 108A of the venous segment 106A. More generally, venous segment can be joined to a segment exiting the patient at a second site, which can be an arterial site as discussed elsewhere herein. The second site can be provided by a surgical procedure that may be minimally invasive. For example, access can be provided through a sub-xiphoid approach to the outside of the heart. A transapical channel can be formed from the outer apex of the heart to the left ventricle. The transapical channel can be disposed within a sheath that is placed through the myocardium. The channel can be of sufficient size for the segment 104A to extend therethorugh. Thus a continuous rail can be provided from the venous access site to the second site outside the patient through the sub-xiphoid access. While the transapical path does not benefit from the anatomical guidance discussed above in connection with FIGS. 1-3, the trajectory from the left atrium, through the mitral valve and out of the apex can be substantially straight in many patients and thus may provide good perpendicularity to the mitral valve annulus, which helps seat the prostheses discussed herein or even a stent mounted prosthetic valve in the mitral valve annulus. Further details of how one would provide transapical access to the left ventricle are discussed in WO2011/017440, which is incorporated by reference in its entirety.

A loop, snare, Shepard's hook tip or other structure for capturing the venous segment 106A can be provided on the arterial segment 104A. The capturing structure is provided such that the venous segment can be withdrawn percutaneously through the arterial access site to create a single, continuous, guidance rail extending from the venous access site, through the heart, to the arterial access site. In other approaches, the arterial and venous segments are joined intravascularly to provide a continuous venous-arterial guide rail. The guidance and ensnaring or joining method may be accomplished using mated surfaces such as a ball and socket, fixation methods or structures such as a threaded connector, or using permanent or electro-magnetically tipped segments that attract when in proximity. Portions of one or both of the tips of the segments 104A, 106A may be radiopaque to facilitate snaring of these components.

In further embodiments, using any one or combination of guidance technique, e.g., echocardiographic, fluoroscopic, or flow-directed guidance, the venous segment guidance rail is placed percutaneously through a venous access site, advanced across a atrial septal aperture, through the mitral valve, left ventricle, aortic valve, ascending aorta, aortic arch, and finally into the descending aorta. From an arterial access site, the arterial segment is placed percutaneously into an arterial access site, and advanced toward the distal tip of the venous segment. Utilizing a snare disposed on the arterial segment or other joining device such as permanent magnets embedded into the distal tips of both venous and arterial segments, the venous segment is ensnared firmly by the arterial segment. As the venous segment is advanced, the arterial segment is withdrawn to guide the venous segment toward and out of the arterial access site. This establishes a continuous guidance rail extending percutaneously from the venous access site to the arterial access site. Or, as noted above, the venous and arterial segments may be joined by permanent magnets, a threaded connection or other low profile joining structure such that the venous and arterial segments can remain in place for advancement of other catheter devices thereover.

Figure 20:
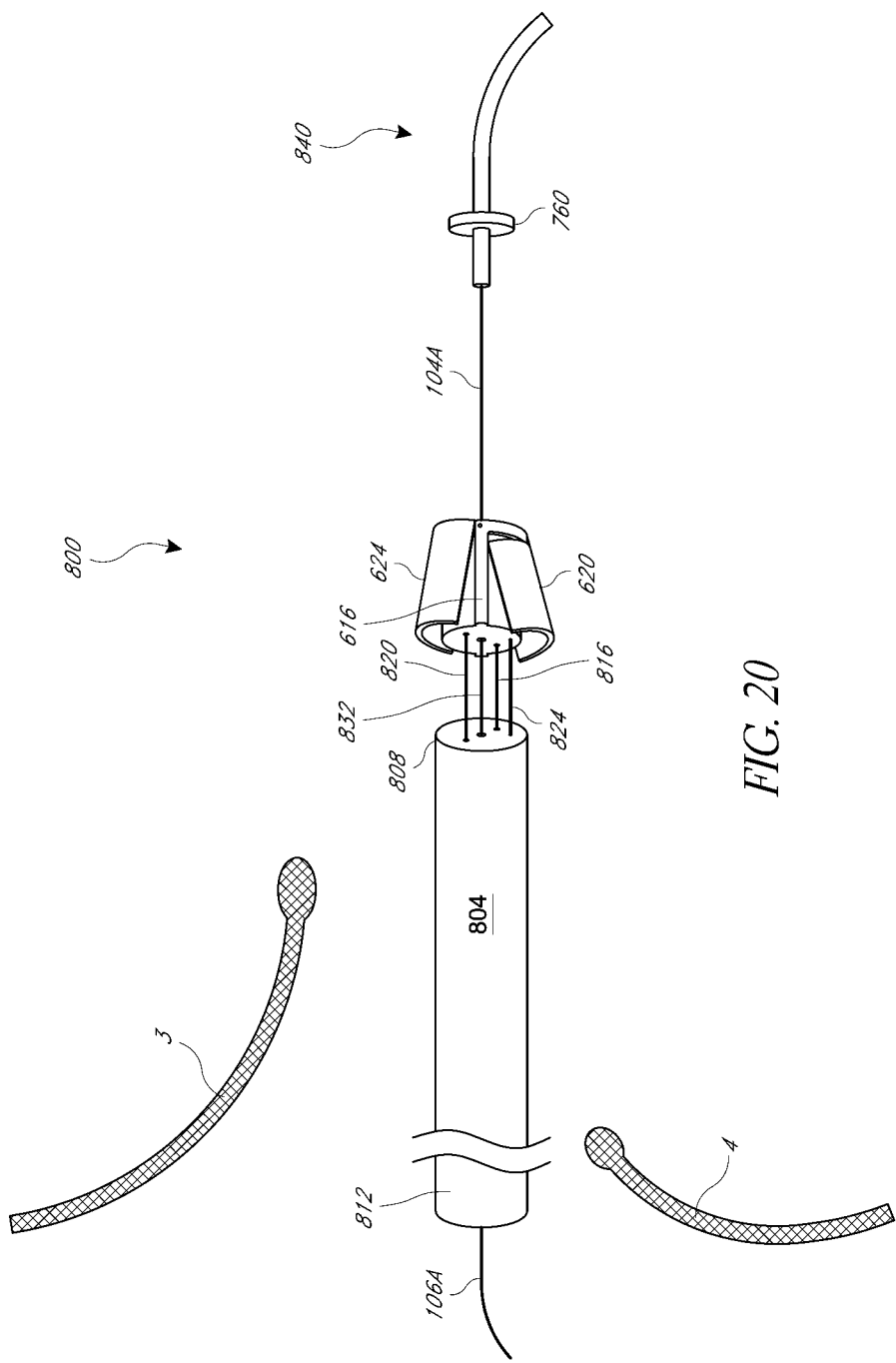
FIG. 20 illustrates part of a system for deploying the prosthesis of FIGS. 16-19.

FIG. 20 illustrates that the prosthesis 600, which may be a metallic cylindrical clip device, can be disposed on a catheter system 800. The catheter system 800 in includes a proximal or venous segment 804 that has a distal tip 808 and a proximal end 812. For simplicity, all of the anatomy is omitted except the anterior and posterior leaflets 3, 4. In certain embodiments, a control rail formed by the segments 104A, 106A is present and controls the trajectory (e.g., position and orientation) of the venous segment 804. Accordingly, the venous segment 804 can be advanced from the venous vasculature and controlled from the venous access site. In other embodiments, the catheter system 800 includes a distal segment coupled with a distal face of the prosthesis 600. The distal segment, if provided, controls of the position and deployment of the prosthesis 600 from arterial access site. Thus various embodiments of the catheter system 800 control deployment of the prosthesis 600 from one or both of a venous access site and an arterial access site. The proximal end 812 of the proximal segment 804 is disposed outside the patient, e.g., exiting a femoral vein or other peripheral vascular segment. The body of the proximal segment 804 is long enough to reach from the peripheral venous site at least to the mitral valve but in certain embodiments through the heart into the arterial vasculature as discussed above. One or a plurality of control elements extend though of a catheter system 800. FIG. 20 shows that one embodiment provides a fluid delivery channel 816 to deliver control fluid to the actuator 704 in driving engagement with the posterior element 620. A fluid delivery channel 820 is provided to deliver control fluid to the lumen 732 and to an actuator disposed in fluid communication with the lumen 732. Control fluid delivered through the fluid delivery channel 820 acts on the actuator to actuate the anterior element 624.

An indexing member 824 can be selectively engaged with the indexing feature 744 to orient the prosthesis 600 about the longitudinal axis there of or relative to the proximal segment 804 or the leaflets 3, 4. The indexing member can be an elongate slender rod or any of the other features discussed hereinabove or another suitable structure.

A push element 832 can be engaged with the threaded recess 740. The push element 832 can extend to the proximal end 812 and to an actuator device to be manipulated by the clinician. In one embodiment, the push element 832 has a lumen that enables the proximal segment to be delivered over a guidewire or rail.

FIG. 20 shows an example of delivery over a rail. In particular, a rail including proximal and distal segments 106A, 104A is established by any of the techniques discussed above. The prosthesis 600 disposed at the end of proximal segment 804 of the catheter system 800 is then advanced over this guidance rail from the venous access site. In other words, in this method, the combination of the proximal and distal segments 106A, 104A form a guide rail and the prosthesis 600 is disposed within a separate catheter that is guided over this rail to the heart. If advanced from the venous side, the catheter system 800 is advanced into the right atrium, across the atrial septum, into the left atrium, and to the mitral valve over the rail formed by the proximal and distal segments 106A, 104A.

The anterior element 620 is posited to face the anterior leaflet 3. Utilizing fluid pressure in the fluid delivery channel 816, the anterior element 620 facing the anterior mitral leaflet 3 is opened and held in the open position. By advancing and withdrawing the catheter carrying the prosthesis 600 along the guidance rail (combination of segments 104A, 106A), the posterior leaflet 4 is directed between the surface 620A of the anterior element 620 and the surface 672 of the base 616, at which point fluid pressure to the anterior element 620 is removed. This allows the anterior element 620 to return to the closed position. Then, utilizing fluid pressure in the fluid deliver channel 820, the anterior element 624 facing the anterior leaflet 3 is opened and held in the open position. The catheter carrying the prosthesis 600 over the guidance rail (104A, 106A) is then manipulated to position the anterior leaflet 3 between the surface 624A of the posterior element 624 and the surface 676 of the base 616, at which point fluid pressure is removed or decreased, allowing the posterior element 624 to return to the closed position. At this point, the anterior and posterior leaflets 3, 4 will be fastened together by the prosthesis 600, and positioned along the guidance rail. After the leaflets 3, 4 have been grasped the push element 832 can be disengaged from the threaded recess 740.

In some methods, the retention member 760 is thereafter applied to the prosthesis 600. In one approach, catheter body 840 is advanced over the guide rail from the arterial access site, e.g., over the distal segment 104A. The catheter body 840 is placed over the guidance rail and advanced toward the prosthesis 600 at the mitral valve. The catheter body 840 can be advanced to be adjacent to the prosthesis 600 and in one approach docks with the distal end 612 of the body 604 (e.g., by a threaded or other secure connection). The retention member 760 is engaged with the catheter body 840. In FIG. 20 the retention member 760 is shown as much larger than the body 840 but would generally be disposed flush on a surface of the body 840. The surface would have an outer diameter approximately the same as or slightly larger than the diameter of the body 604 of the prosthesis 600. A sheath (not shown) or other pushing rod or member disposed over or within the catheter body 840 can be brought into engagement with a proximal face of the retention member 760 and when urged distally on the catheter body 840 can cause the retention member 760 to be urged off of the catheter body 840 onto the prosthesis 600. Thus the retention member 760 can be urged over the distal end 612 of the body 604 to a position around the grasping element 620, 624 to the position shown in FIG. 16. The retention member 760 is configured to hold both of the grasping element 620, 624 against the body 616 in the closed position and protect against inadvertent clip opening. The catheter body 840 is then withdrawn from the body. The distal end 808 of the proximal segment 804 is then detached from the prostheses 600, and withdrawn from the body. The guidance rail including the proximal and distal segments 106A, 104A can then be withdrawn from the body.

The prosthesis 600 has many advantages. For example, the configuration of the prosthesis 600 allows independent actuation of each gripping element 620, 624. Although the prosthesis 600 can grip the leaflets 3, 4 simultaneously, this feature allow for independent and in some cases sequential capture of each leaflet 3, 4. This makes grasping the mitral valve much simpler than where multiple gripping elements simultaneously grip the leaflets. Because the prosthesis 600 is optimally placed in a beating heart, any features that simplify the procedure can greatly improve patient outcomes and hasten recovery.

Furthermore, the arcuate (e.g., semicircular) profile of the gripping members 620, 624 allows more leaflet material to be clipped or grasped between the surfaces 620A, 624A, and the surface 672, 676 respectively than if the engaging surfaces were less curved or flat. By lengthening the engagement area, the prosthesis 600 may provide valvular sufficiency without any additional devices. In certain conventional techniques, to fully treat certain patients multiple clips are required. The curved profile is one of the features of the prosthesis 600 that will enable patients with advanced disease to be treated with a single prosthesis in some embodiments.

Also, embodiments with fluid, e.g., hydraulic or pneumatic, actuation enable the prosthesis 600 to be very simple to operate. The proximal segment 804 is advanced through the valve and after the gripping element(s) 620, 624 are opened, the catheter 804 is withdrawn to a valve leaflet gripping position. After both leaflets are gripped, the threaded push element 832 engaged with the recess 740 is unthreaded from the recess 740 by hand rotation of the member. The indexing member 824 or other counter-torque device is used to prevent the prosthesis 600 from rotating within the delivery catheter. This reduces, minimizes or eliminates torque from being applied to the valve leaflets 3, 4. The control fluid can be advanced into the channel 700 with a syringe or simple pump or other flow control device.

The syringe can be hand operated, providing direct tactile feedback to the clinician. Using a flow control device with direct tactile feedback is advantageous in enabling the clinician to automatically know from feel the state of the prosthesis 600. This approach is superior to robotic controllers that, while precise, prevent the clinician from directly and immediately being able to confirm the status of the device inside the patient's heart. Because the clinician has better information at the bedside, the procedure can be faster and safer.

FIGS. 21-25C illustrate a system 856 for deploying a cardiac valve repair device, e.g., a mitral valve repair device including a prosthesis 858. The delivery system 856 and the prosthesis 858 are similar to those hereinbefore described while embodying other features described herein. The delivery system 856 provides an elongate catheter structure that can extend from a peripheral venous site to a peripheral arterial site. The delivery system 856 can have a variety of control devices to steer and actuate the prosthesis 858, to actuate the prosthesis 858 and to separate portions of the catheter structure from the prosthesis 858.

In certain embodiments the delivery system 856 includes a proximal catheter portion 870 and a distal catheter portion 872. The proximal catheter portion 870 is located proximal of a proximal face of the prosthesis 858. The proximal face is located at a proximal end 860 of the prostheses 858. More specifically the proximal catheter portion 870 has a proximal end 884, a distal end 888, and an elongate body 890 extending therebetween. The distal end 888 is located at an interface between the proximal catheter portion 870 and the prosthesis 858.

Figure 21:
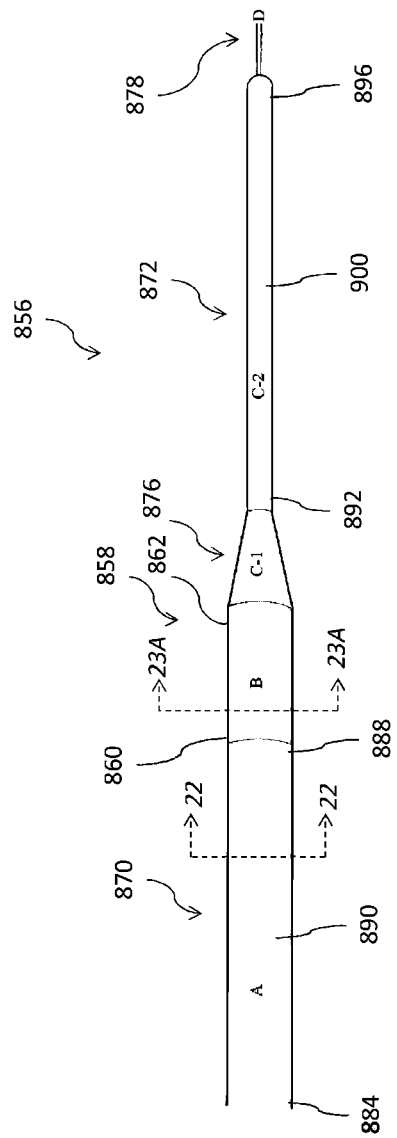
FIGS. 21 and 22 illustrate further features of a system for deploying a mitral valve repair device.

FIG. 21 shows that the interface can be at a location where the distal end 888 and the proximal end 860 are directly coupled. As shown, a continuous outer profile is provided between a proximal end 860 of the prosthesis 858 and the distal end 888 of the proximal catheter portion 870. As discussed above, the elongate body 890 can be configured to traverse the vasculature between a peripheral venous location and the chamber of the heart. In particular, the elongate body 890 can be placed through the vena cava into the right atrium and can project downward towards the mitral valve space. The continuous outer profile can facilitate smooth passage through narrows in the delivery path, e.g., through valves and through an aperture formed in the atrial septum as discussed below. The distal end 888 can be detachably coupled with the proximal end 860 of the prosthesis 858 at this interface.

The distal catheter portion 872 also includes a proximal end 892, a distal end 896, and an elongate body 900 extending therebetween. The distal catheter portion 872 is located distal of a distal face of the prosthesis 858. The elongate body 900 is configured to be placed in the vasculature between heart and a peripheral arterial site. For example, the elongate body 900 can extend through the left ventricle across the aortic valve into the aorta. The elongate body 900 can further extend through the ascending aorta, the descending aorta, and into a peripheral blood vessel, such as the femoral artery. The distal catheter portion 872 preferably has a smaller profile, e.g., cross-section, than the proximal catheter portion 870. The smaller cross-section enables the delivery system 856 to extend into or out of a small peripheral artery, e.g., an artery that is smaller than the venous access point used for the proximal catheter portion 870. The smaller cross-section reduces or eliminates the need for a cut-down of the peripheral artery and/or reduces or minimizes the risk of the blood vessel tearing around a percutaneous access sheath through which the distal catheter portion 870 may access the peripheral artery.

The delivery system can also include a tapered portion 876. In the illustrated embodiment, the tapered portion 876 is disposed between the distal catheter portion 872 and the prosthesis 858. The tapered portion 876 facilitates delivery of the prosthesis 858 by easing access through a narrows, such as a created or natural opening e.g., through cardiac valves and/or a puncture in an atrial septum). The tapered portion 876 can dilate structures around one or more narrows or openings in wall(s) of the heart. Each of the proximal catheter portion 870, the distal catheter portion 872, and the tapered portion 876 are configured to he advanced over an elongate guidewire 878 as discussed further below.

The tapered portion 876 can be disposed between the proximal end 892 of the distal catheter portion 872 and a distal end 862 of the prosthesis 858. The tapered portion 876 can provide a progressively larger outer profile in a proximal direction from at or adjacent to the proximal end 892 of the distal catheter portion 872. A proximal end or portion of the tapered portion 876 can be detachably coupled with or otherwise separable from the distal end 862 of the prosthesis 858. The proximal face of the tapered portion 876 is configured to provide a secure connection of the tapered portion to the prostheses 858 for delivery and manipulation of the prosthesis. The proximal face of the tapered portion 876 is able to separate from the prostheses 858 without disrupting the prostheses after the prostheses has been secured to the valve leaflets. Aspects of the detachable coupling are discussed in further detail below.

In some cases it is important to keep the size of the arterial access site as small as possible. For such cases, it may be preferable to avoid removing the tapered portion 876 through an arterial access site able to accommodate the largest profile (e.g., diameter) of the tapered portion 876. In one variation, the tapered portion 876 is configured to be removeably coupled with the distal catheter portion 872. This allows the arterial access site to be configured to be just large enough to accommodate the distal portion 872, for example smaller than the largest profile (e.g., diameter) of the tapered portion 876. Any device described herein can be placed between the distal end of the tapered portion 876 and the proximal end of the distal catheter portion 872 to facilitate detachment. The tapered portion 876 can be integrated into the prosthesis 858. In another variation, the tapered portion 876 can be selectively expandable such that it can be actuated to the tapered configuration for passing the system 856 through a narrows and thereafter de-actuated to allow the tapered portion 876 to have a lower profile, e.g., a profile about the same as that of the distal portion 872. This allows the tapered portion 876 to provide a dilating function, but enables the tapered portion to exit through a small arterial access site, through a port disposed in the arterial vasculature having an access lumen not substantially larger than the profile of the distal portion 872. In one version, the outer surface of the tapered portion 876 at least partially encloses a cavity that can be filled with an inflation medium through a lumen (not shown) in the distal portion 872. Then the cavity is filled, the outer surface takes on the profile illustrated in FIGS. 24B and 24C.

In further variations, the distal catheter portion 872 is eliminated, which allows the arterial access site to be made much smaller because distal catheter portion 872 is not retained through the arterial access site during the procedure. In one arrangement, the proximal catheter portion 872, prostheses 858, and tapered portion 876 are advanced over the guidewire 878, which extends to an arterial access site and outside the body. The guidewire 878 can facilitate positing of the prostheses 858 as discussed above and can be removed from the venous or arterial access site after the procedure is complete. In one variation suitable for this technique, the tapered portion 876 is replaced with a conventional dilator for providing access between the right and left atria. In another variation suitable fort this technique, the tapered portion 876 is integrated into the prostheses 858.

In further variations, the arterial access site is completely eliminated. For example, the guidewire 878 can be provided with a small balloon configured to be carried by blood flow to an artery, including the aorta or a more distal arterial vascular bed. The balloon becomes lodged therein to a sufficient extent to facilitate positioning as discussed above. The procedure can be performed to place the prostheses 858. Thereafter, the balloon on the guidewire 878 can be deflated to disengage the artery in which it is lodged. Thereafter, the guidewire 878 can be removed proximally thorough the lumen 902B and out of the patient's body at the venous access site. The tapered portion 876 could be replaced with a conventional dilator or integrated into the prosthesis 858 in systems suitable for a single access site procedure.

Figure 22:
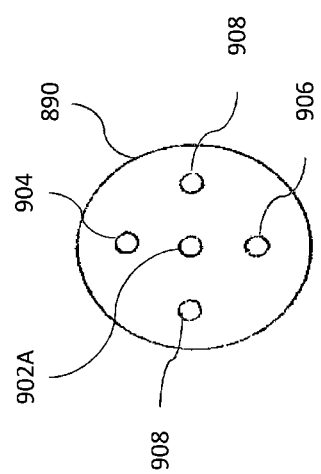

FIG. 22 illustrates the proximal catheter portion 870 in cross-section, showing a plurality of controlled lumens disposed in the body. A guidewire lumen 902A is disposed in a central portion of the proximal catheter portion 870. The guidewire lumen 902A forms a part of a continuous guidewire passage of the system 856 and the prosthesis 858, which continuous passage comprises several separable lumen segments. This permits the guidewire 876 to extend from the distal end 896 and through a lumen segment 902C in the elongate body 900 of the distal catheter portion 872, through the tapered portion 876, through a lumen segment 902B in the prosthesis 858 and into the lumen 902A. The guidewire 878 can thus traverse the entire system 856 during some portions of the procedure.

A steering lumen 904 preferably is provided in at least partially through the proximal catheter portion 870. For example, the steering lumen 904 can be provided at a peripheral location relative to the location of the guidewire lumen 902A. The steering lumen 904 can house a wire or other tension member configured to adjust the position, orientation, or angle of at least the distal end 888 of the proximal catheter portion 870. This adjustment enables the position, orientation, or angle of the prosthesis 858 to be adjusted as well. In some embodiments, the steering lumen 904 houses a member that can act in tension or in compression. Adjustment of the position, orientation, or angle of the prosthesis 858 can be provided by deflecting the distal end 888 of the proximal catheter portion 870 by applying a force to the tension and or compression member. Another degree of adjustment can be provided by rotating the proximal catheter portion 870 about its longitudinal axis such that the deflection of the distal end 888 can be adjusted relative to a landmark of the patient, e.g., relative to the line of coaptation of the mitral valve or relative to specific aspects of the leaflets.

In other embodiments, the delivery system 856 can include a steered catheter portion that can be manipulated using two or more tensile wires to achieve deflection in two or more directions. In other embodiments, one tensile wire in a catheter portion can be combined with a pre-bent radius tip to achieve deflection in two directions. In other embodiments, three tensile wires in a catheter portion can be used alone or in combination with a pre-bent radius tip to achieve deflection in three or more directions. In other embodiments, four tensile wires in a straight catheter can be used to achieve deflection in four or more directions. In other embodiments, a rotatable segmented tip can be used to achieve deflection in two or more directions.

FIG. 22 shows that the proximal catheter portion 870 can further include a control lumen 906 for selectively decoupling or detaching the proximal catheter portion 870 from the proximal end 860 of the prosthesis 858. The control lumen 906 can house any of the control members or mechanisms discussed above. Further examples of low-profile control mechanisms are discussed below in connection with FIGS. 25A-25C.

FIG. 22 further shows that the proximal catheter portion 870 can include a plurality of control lumens 908 for actuating features of the prosthesis 858. The control lumens 908 preferably are configured to be placed in fluid communication with a control fluid, such as any of those hereinbefore described. The control fluids can be forced into the lumens 908 to pressurize the lumens. When the lumens are pressurized, features of the prosthesis 858, such as clip structures or grasping elements can be actuated as discussed below. FIGS. 21-23C illustrated that in various embodiments a plurality of control lumens 908 is provided in the elongate body 890 such that one control lumen can be placed in fluid communication with each clip structure or grasping element. This provides the advantage of being able to actuate each clip independently. As a result, either one of the anterior or posterior mitral valve leaflets can be approached and grasped first, followed by the other of the anterior or posterior mitral valve leaflet. This allows a clinician to simplify the procedure by permitting the clinician to grasp each leaflet independently.

FIGS. 23A-23C illustrate further features of certain embodiments of the prosthesis 858. The prosthesis 858 can include features of the prosthesis 600 discussed above and may include any of the following features. In particular, the prosthesis 858 includes an elongate arcuate body 912, a base 914, an anterior leaflet grasping element 916, and a posterior leaflet grasping element 918. The grasping elements 916, 918 are shown as having generally flat tissue grasping faces but can have curved faces as discussed above in connection with the prostheses 600. As discussed above, the curved faces enhance the tissue grasping capability of the prosthesis 858. Also, the grasping elements 916, 918 can be identical or can be different from each other as discussed above in connection with the prostheses 600. The base 914 can be disposed at a central portion of the prosthesis 858 and can include a plurality of lumens extending therethrough. The base 914 includes a lumen 902B configured to receive the guidewire 878, as discussed above, as well as lumens 920 configured to receive portions of the grasping elements 916, 918. The lumens 920 can take any suitable configuration, but preferably are noncircular to reduce or minimize twisting of the grasping elements 916, 918 relative to the base 914. The base 914 also preferably has a control surface 922 facing toward each of the grasping elements 916, 918.

The grasping elements 916, 918 preferably are slidably engaged to the base 914. For example, the grasping elements 916, 918 each can include a control member 921 extending from a distal end toward a proximal end thereof. The control members 921 preferably are each configured to be received within one of the lumens 920. The control members 921 can be retained within the lumen 920 in a manner that permits the control members to slide axially relative to the base 914 but provides for retaining the fluid for actuating the grasping element 916 within a proximal portion of the lumen 920, e.g., a portion disposed proximally of the control member 921. For example, a seal can be provided between the control member 921 and the inner wall of the lumen 920 to prevent significant leakage of actuating fluid. The grasping element 916 preferably also includes a grasping member 924 having a grasping face 925 disposed thereon. The grasping member 924 and grasping face 925 preferably are coupled with the control member 921 such that when the control members 921 slide within the lumens 920 the grasping member 924 also slides over an outer surface of the base 914.

Preferably the coupling between the control member 921 and the grasping member 924 is elastic such that the grasping member 924 can deflect away from the base 914 in one state of the grasping element 916 and can thereafter be resiliently urged back toward the base 914 in another state. In one embodiment the grasping member 924 and the control member 921 are coupled as a single unitary or monolithic body, similar to a living hinge.

The grasping element 924 preferably also has a control surface 928 disposed thereon. The control surfaces 922, 928 interact to control the opening and closing movements of the grasping member 924. With reference to FIG. 23B, the prosthesis 858 is configured to have a closed configuration in which control surfaces 922, 928 are nested within each other providing close contact between the gripping face 925 and a surface of the base 914. The gripping faces 925 or other aspects of the grasping member 924 can be textured, coated, covered as with fabric (e.g., EPTFE or other biocompatible inert material), or otherwise processed to maximize friction to the clipped tissue surface, whilst preventing puncture. FIG. 23C shows that the prosthesis 858 has an open configuration in which the control surfaces 922, 928 are displaced relative to another such that these surface no longer nest, but rather protruding portions of the control surfaces 922, 928 are axially aligned. Such axial alignment pushes the grasping member 924 away from the base 914 as shown in FIG. 23C.

As noted above, the grasping members 924 and the control member 921 preferably are elastically coupled, e.g., joined at an elastic structure. An elastic region can be disposed adjacent to the distal end of each of the grasping elements 916, 918. The elastic region can be configured such that as a force is applied, e.g., from a fluid pressure in the control lumens 908 is reduced, strain energy is stored in the elastic region between the grasping member 924 and the control member 921 upon urging the control member 921 and the grasping member 924 distally. The strain energy can be released upon reducing the fluid pressure in the control lumens 920 causing proximal movement of the grasping elements 916, 918. As these structures move proximally, the axially aligned protruding portions of the control surfaces 922, 928 (as in FIG. 23C) move out of alignment. When the protruding or convex portion of the control surface 922 is aligned with a concave feature of the control surface 928 the grasping element 924 can come into adjacency with the base along the entire length of the grasping member 924. Stated another way, a spring force in the grasping elements 916, 918 urges the grasping elements 916, 918 proximally relative to the base 914 to a position where the control surfaces 922, 928 are able to nest together along their length causing an opening between the grasping member 924 and the base 914 to be closed. The spring force is configured such that the grasping member 924 is urged against the base 914 with sufficient force or pressure to hold an active mitral valve leaflet.

FIGS. 24A-24C show further features of the tapered portion 876 that facilitate attachment to and detachment of the tapered portion 876 from a distal portion of the prosthesis 858. The tapered portion 876 includes a distal end 932 and a proximal end 934. The profile of the tapered portion decreases and a distal direction between the proximal end 934 and the distal end 932, e.g., from the proximal end 934 to the distal end 932. The proximal end 934 includes an interface 936 for mechanically engaging with the distal end 862 of the prosthesis 858. The interface 936 can take any suitable form, but preferably is low profile such that the interface 936 does not enlarge the outer diameter of the delivery system 856 at or adjacent to the distal end 862 of the prosthesis 858. In one embodiment, the interface 936 includes a plurality of prongs 938 projecting from a proximal face of the proximal end 934 of the tapered portion 876. The prongs 938 can be configured as elongate wire like projections that extend proximally and can be received within corresponding recesses disposed on a distal face of the distal end 862 of the prosthesis 858. The prongs 938 and corresponding recesses on the prosthesis 858 are engaged for delivery of the prostheses 858. The engagement between the prong and recess is configured with sufficient strength to prevent the tapered portion 876 and the prosthesis 858 from becoming disengaged during advancement of the delivery system 856 through the venous vasculature, through the heart, and through the arterial vasculature, and also during positioning of the prosthesis 858 at or adjacent to the plane of co-optation of the mitral valve.

The interface 936 preferably also includes a low profile detachment actuator 940. In one embodiment, the low profile detachment actuator 940 includes a proximally oriented recess 942 formed in the tapered portion 876. The recess 942 is sized to house a small inflatable member 944. The recess 942 can be present in the non-expandable and in the expandable versions of the tapered portion 876. The inflatable member 944 is in fluid communication with an inflation lumen 946 that extends from a proximal end of the recess 942 through the elongate body 900 to a distal end of the distal catheter portion 872. The lumen 946 can be placed into fluid communication with a source of inflation media which can be directed into the inflatable member 944 to larger inflate the member.

FIG. 24C shows that when the inflatable member 944 is inflated, a proximal face 948 of the inflatable member 944 is disposed proximally of the proximal end 934 of the tapered portion 876. FIG. 24C shows the detachment actuator 940 separate from the prosthesis 858. However, if the tapered portion 876 is coupled with the prosthesis 858 inflated state of FIG. 24C will provide that the proximal face 948 of the inflatable member 944 comes into contact with and applies a force or a pressure to a distal face of the prosthesis 858. The extent of inflation of the inflatable member 944 and the rigidity of the proximal face 948 of the inflatable member are configured such that the force or pressure applied to the distal face of the prosthesis 858 exceeds the force of securement between the prongs 938 (or similar structure) and the prosthesis. The result is that upon inflation of the inflatable member 944, the tapered portion 876 is separated from the prosthesis 858.

FIGS. 24A-24C also show that the lumen 902C is disposed through the tapered portion 876. The inflatable member 944 can be configured in a number of ways to accommodate the presence of the guidewire 878. For example, the inflatable member 944 can have an annular shape such that a lumen extends through an inner periphery of the inflatable member 944. In another embodiment, inflatable member 944 is disposed in a space around the guidewire 878. For example, the guidewire can be preloaded into the delivery system 856 as shown in FIG. 21. In another embodiment, inflatable member 944 provides a distal face that is configured to resist puncture such that upon urging the proximal end of the guidewire 878 against the distal face, inflatable member 944 is pushed aside to permit the guidewire to pass.

FIGS. 25A-25C illustrate a low profile detachment actuator 952 configured to be manipulated from at or adjacent to the proximal end 884 of the proximal catheter portion 870. The detachment actuator 952 is an example of a non-threaded connection that can be provided to enable a clinician to selectively decouple the distal end 862 of the proximal catheter portion 870 from the proximal end 860 of the prosthesis 858.

FIGS. 25A-25C illustrate a portion of a proximal face 954 of the prosthesis 858. A recess 956 is illustrated extending distally from the proximal face 954. Between the proximal face 954 and a distal end 958 of the recess 956 an engagement zone 960 is provided. The engagement zone 960 can take any suitable form, and in the illustrated embodiment includes a concave recess. The concave recess extends transversely away from the longitudinal axis of the recess 956.

The engagement of the detachment actuator 952 is provided by a locking member 962 that is trapped partly in the concave recess. In one embodiment, the locking member 962 is a convex member that can be partly received in the concave recess of the engagement zone 960. The convex member spans the concave recess and also spans across a locking sleeve 964. An elongate member 966 is moveable within the locking sleeve 964 between a locked position and an unlocked position. When in the locked position, the elongate member 966 traps the locking member 962 within the engagement zone 960. In one example, the elongate member 966 has a stepped configuration such that at a first position a surface of the elongate member 966 is spaced apart from the concave recess by a distance D1 (see FIG. 25A) about equal to the width, e.g., diameter, of the locking member 962. The distance may be greater than the width of the locking member 962 but by an amount that is less than the depth of the concave recess of the engagement zone 960. The stepped configuration can further have a second position in which the surface of the elongate member is spaced apart from the concave recess by a distance D2 (see FIG. 25B) greater than the width, e.g., diameter, of the locking member 962. In the second position the locking member 962 can move out of the concave recess of the engagement zone 960 permitting the locking sleeve 964, the elongate member 966 and the locking member 962 to be withdrawn.

The low profile detachment actuator 952 is partly housed in the proximal catheter portion 870 and partly in the prosthesis 858. For example, in an engaged configuration a distal portion of the locking sleeve 964 and locking member 966 are received in the prostheses 858 and a proximal length extends through the control lumen 906. In an unengaged configuration, the locking member 962 is freed from the engagement zone 960 and is free to be removed from the prostheses 858 by shifting the position of the locking sleeve 964 and elongate member 966 within the control lumen 906.

A method facilitated by the low profile detachment actuator 952 of FIGS. 25A-25C provides that upon delivery of the prosthesis 858 through the vasculature to the heart, the locking sleeve 964 and elongate member 966 are positioned as in FIG. 25A to trap the locking member 962 in the engagement zone 960. To separate the prosthesis 858 from the proximal catheter portion 870 of the delivery system 856, the elongate member 966 is withdrawn within the lumen of the locking sleeve 964. This permits the locking member 962 to disengage from the engagement zone 960 as shown in FIG. 25B. The low profile detachment actuator 952 can thereafter be withdrawn completely from the prostheses 858 by proximal movement relative to the prosthesis 858. In one technique the locking member 962 is trapped in the locking sleeve 964 by moving the elongate member 966 distally within the locking sleeve 964 to retain the locking member 962 safely in a distal length 970 of the locking sleeve 966.

Other structures for securing proximal and distal catheter portions to the prosthesis 858 can include one or more of press fit, directly applied tension or compression by a wire, a snap-together retaining clip, an internal wire, a threaded connector that is separable by externally applied torque, and/or solid fastening structures such as wires or welds that can controllably dissolved, for instance, via controlled dissolution or corrosion with applied voltage.

Although the present invention has been disclosed with reference to certain specific embodiments of devices and methods, the inventors contemplate that the invention more broadly relates to methods disclosed above, such as those useful for orienting a catheter with respect to an anatomical structure, as well as performing diagnostic and/or therapeutic procedures in the heart or adjacent the heart. Accordingly, the present invention is not intended to be limited to the specific structures and steps disclosed herein, but rather by the full scope of the attached claims.

What is claimed is:

1. A system for deploying a mitral prosthesis, comprising:
an elongate catheter body assembly comprising a venous portion and an arterial portion having a length disposed between a proximal end of the arterial portion and a distal end of the arterial portion, the elongate catheter body assembly sized to extend from a peripheral venous access site to a heart and from the heart to a peripheral arterial access site;
a mitral prosthesis disposed between and coupled to the venous portion of the elongate catheter body assembly and the arterial portion of the elongate catheter body assembly to provide an outer profile defined by an outer surface of the venous portion, an outer surface of the mitral prosthesis, and an outer surface of the arterial portion, wherein a distal end of the venous portion is coupled to a proximal end of the mitral prosthesis radially inward of the outer profile and a proximal end of the arterial portion is coupled to a distal end of the mitral prosthesis radially inward of the outer profile, wherein the arterial portion of the elongate catheter body assembly is configured to detachably couple from the distal end of the mitral prosthesis, wherein when the system is disposed in a patient with the mitral prosthesis positioned at a mitral valve for deployment, the length of the arterial portion extends from the heart to the peripheral arterial access site; and
a first control device disposed in the venous portion of the elongate catheter body assembly to facilitate angulation of the mitral prosthesis from a venous end;
wherein the mitral prosthesis can be positioned by manipulation of one or both of the venous portion and the arterial portion and the mitral prosthesis can be angled by the first control device.

2. The system of claim 1, wherein the first control device comprises a tension member disposed in a peripheral lumen of the venous portion.

3. The system of claim 1, further comprising a second control device disposed in the venous portion to facilitate remote deployment of each of a plurality of grasping elements of the mitral prosthesis.

4. The system of claim 1, further comprising a detachment actuator configured to separate the mitral prosthesis from at least one of the venous portion and the arterial portion of the elongate catheter body assembly.

5. The system of claim 1, wherein the mitral prosthesis includes a base and at least one tissue grasper.

6. The system of claim 5, wherein the at least one tissue grasper is covered by a fabric material.

7. The system of claim 1, further comprising a guidewire configured to extend through the venous portion of the elongate catheter body assembly from the venous end to support an anchor portion of the elongate catheter body assembly.

8. The system of claim 1, wherein the arterial portion comprises a tapered portion coupled to the mitral prosthesis and the arterial portion, the tapered portion configured to provide a progressively smaller profile in a direction from the mitral prosthesis toward a distal end of the arterial portion.

9. The system of claim 8, wherein a proximal face of the tapered portion is configured to detach from the mitral prosthesis without disrupting a securement of the mitral prosthesis to a heart valve leaflet.

10. The system of claim 8, wherein the tapered portion is integrated into the mitral prosthesis.

11. The system of claim 1 further comprising:
the mitral prosthesis, comprising:
an elongate body, wherein the distal end comprises a distal interface and the proximal end comprising a proximal interface, the distal interface adapted to reversibly couple with the arterial portion of the elongate catheter body assembly while the proximal interface remains coupled to the venous portion of the elongate catheter body assembly;
an arcuate anterior leaflet grasping element articulated at the distal end of the elongate body, the arcuate anterior leaflet grasping element being movable between an open position and a closed position; and
an arcuate posterior leaflet grasping element articulated at the distal end of the elongate body, the arcuate posterior leaflet grasping element being movable between an open position and a closed position.

12. The system of claim 11, wherein the arcuate anterior leaflet grasping element is configured to be actuated independently of the arcuate posterior leaflet grasping element.

13. The system of claim 11, wherein when the arcuate posterior leaflet grasping element is in the closed position the arcuate posterior leaflet grasping element is received in a space at least partially bounded by a base of the elongate body.

14. The system of claim 11, wherein at least one of the arcuate anterior leaflet grasping element and the arcuate posterior leaflet grasping element comprises a control member disposed in a channel, a grasping face, and an elastically deformable region coupled with the grasping face and the control member.

15. A system for deploying a mitral prosthesis, comprising:
an elongate catheter body assembly comprising a venous portion and an arterial portion, the elongate catheter body assembly sized to extend from a peripheral venous site, through a heart, to a peripheral arterial site and when so extended, the venous portion traverses the peripheral venous site while the arterial portion traverses the peripheral arterial site;
a mitral prosthesis disposed between and coupled to the venous portion of the elongate catheter body assembly and the arterial portion of the elongate catheter body assembly to provide an outer profile defined by an outer surface of the venous portion, an outer surface of the mitral prosthesis, and an outer surface of the arterial portion, wherein a distal end of the venous portion is coupled to a proximal end of the mitral prosthesis radially inward of the outer profile and a proximal end of the arterial portion is coupled to a distal end of the mitral prosthesis radially inward of the outer profile, wherein the arterial portion of the elongate catheter body assembly is configured to detachably couple from the distal end of the mitral prosthesis; and
a first control device disposed in the venous portion of the elongate catheter body assembly to facilitate angulation of the mitral prosthesis from a venous end;
wherein the mitral prosthesis can be positioned by manipulation of one or both of the venous portion and the arterial portion and the mitral prosthesis can be angled by the first control device,
wherein the arterial portion comprises a tapered portion coupled to the mitral prosthesis and the arterial portion, the tapered portion configured to provide a progressively smaller profile in a direction from the mitral prosthesis toward a distal end of the arterial portion, and
wherein an outer surface of the tapered portion encloses an expandable cavity that can be filled with an inflation medium.

16. A system for deploying a mitral prosthesis, comprising:
a distal portion, a proximal portion, and a length disposed between the distal portion and the proximal portion, the length sized to extend from a peripheral venous access site to a heart and from the heart to a peripheral arterial access site;
a mitral prosthesis disposed between a proximal end of the distal portion and a distal end of the proximal portion, wherein the distal end of the proximal portion is coupled to a proximal end of the mitral prosthesis and the proximal end of the distal portion is coupled to a distal end of the mitral prosthesis to provide a continuous outer profile defined by an outer surface of the proximal portion, an outer surface of the mitral prosthesis, and an outer surface of the distal portion when the system is introduced into a delivery path and as the mitral prosthesis is advanced to a deployment location, wherein when the system is disposed in a patient with the mitral prosthesis positioned at a mitral valve for deployment. a length of the distal portion extends from the heart to the peripheral arterial access site; and
a detachment actuator configured to separate the proximal end of the distal portion from the distal end of the mitral prosthesis,
wherein the mitral prosthesis can be positioned by manipulation of one or both of the distal portion and the proximal portion of the system.

17. The system of claim 16, further comprising a control device disposed in the proximal portion to facilitate angulation of the mitral prosthesis.

18. The system of claim 16, wherein the distal portion comprises a tapered portion coupled to the mitral prosthesis, the tapered portion configured to provide a progressively smaller profile in a direction from the mitral prosthesis toward a distal end of the distal portion.

19. The system of claim 18, wherein a proximal face of the tapered portion is configured to detach from the mitral prosthesis without disrupting a securement of the mitral prosthesis to a heart valve leaflet.

* * * * *

UNITED STATES PATENT AND TRADEMARK OFFICE
CERTIFICATE OF CORRECTION

PATENT NO. : 12,279,956 B2  
APPLICATION NO. : 16/999827  
DATED : April 22, 2025  
INVENTOR(S) : Robert James Siegel Page 1 of 1

It is certified that error appears in the above-identified patent and that said Letters Patent is hereby corrected as shown below:

In the Specification

Column 2, Line 10, delete "the patients circulatory," and insert -- the patient's circulatory, --.

Column 2, Line 23, delete "a patients recovery" and insert -- a patient's recovery --.

Column 3, Line 8 (approx.), delete "downward, arras of" and insert -- downward, arms of --.

Column 6, Line 41, delete "push clement." and insert -- push element. --.

Column 14, Line 43, delete "may he incorporated" and insert -- may be incorporated --.

Column 23, Line 2, delete "compressive three is" and insert -- compressive force is --.

Column 28, Line 8, delete "opening e.g., through" and insert -- opening (e.g., through --.

Column 28, Line 13, delete "to he advanced" and insert -- to be advanced --.

Column 28, Line 54, delete "site, through a" and insert -- site, e.g., through a --.

Column 29, Line 52, delete "tension and or compression" and insert -- tension and/or compression --.

In the Claims

Column 36, Claim 16, Line 52 (approx.), "for deployment. a" and insert -- for deployment, a --.

Signed and Sealed this  
Nineteenth Day of August, 2025

Coke Morgan Stewart  
*Acting Director of the United States Patent and Trademark Office*